(12) United States Patent
Ziegler et al.

(10) Patent No.: US 9,416,458 B2
(45) Date of Patent: Aug. 16, 2016

(54) METHODS FOR DETERMINING GREEN ELECTRODE ELECTRICAL RESISTIVITY AND METHODS FOR MAKING ELECTRODES

(71) Applicant: ALCOA INC., Pittsburgh, PA (US)

(72) Inventors: Donald P. Ziegler, Lower Burrell, PA (US); John Secasan, Murrysville, PA (US)

(73) Assignee: Alcoa Inc., Pittsburgh, PA (US)

( * ) Notice: Subject to any disclaimer, the term of this patent is extended or adjusted under 35 U.S.C. 154(b) by 491 days.

(21) Appl. No.: 14/139,444

(22) Filed: Dec. 23, 2013

(65) Prior Publication Data

US 2014/0183770 A1    Jul. 3, 2014

Related U.S. Application Data

(60) Provisional application No. 61/747,742, filed on Dec. 31, 2012, provisional application No. 61/783,933, filed on Mar. 14, 2013.

(51) Int. Cl.
*G01R 27/14* (2006.01)
*C25C 1/02* (2006.01)
*G01N 27/04* (2006.01)
*G01N 33/22* (2006.01)

(52) U.S. Cl.
CPC ............... *C25C 1/02* (2013.01); *G01N 27/041* (2013.01); *G01N 33/222* (2013.01)

(58) Field of Classification Search
CPC .......... C25C 1/02; G01N 27/041; G01R 27/14
See application file for complete search history.

(56) References Cited

U.S. PATENT DOCUMENTS 7,576,534 B2    8/2009   Audet et al.

OTHER PUBLICATIONS

Dickin, F. et al., "Electrical resistance tomography for process applications", Meas. Sci. Technol., vol. 7 (1996) pp. 247-260 (abstract only).
Fischer, W. K. et al., "Determining Prebaked Anode Properties for Aluminum Production", Journal of Metals, Nov. 1987, pp. 43-45 (abstract only).
International Preliminary Report on Patentability, International Application No. PCT/US2013/077597, issued Jun. 30, 2015.
Nguyen, Q. C., "Electrical Resistivity Measurements of Carbon Electrodes", Proceedings of the 17th Biennial Conference on Carbon, Jun. 16-21, 1985, pp. 27-28.
Tkac, M. "Porosity Development in Composite Carbon Materials during Heat Treatment", PhD Thesis, Norwegian University of Science and Technology, Apr. 2007.

*Primary Examiner* — James Sanders
(74) *Attorney, Agent, or Firm* — Greenberg Traurig, LLP

(57) ABSTRACT

The instant disclosure is directed towards methods of determining green electrode quality via electrical resistivity measurements on green electrode forms (e.g. prior to baking) The instant disclosure is directed towards methods of making electrodes, utilizing the electrical resistivity measurement(s) from green anodes to monitor and if necessary, adjust electrode processing parameters (e.g. composition, mixing parameters, forming parameters, or baking parameters).

16 Claims, 18 Drawing Sheets

BAKED AND GREEN ANODE COMPARISON:

| LOCATION | | RESISTIVITY ($\mu\Omega m$) | |
|---|---|---|---|
| | | BAKED ANODES | GREED ANODES |
| STUB HOLE: | | | |
| | A | 57.9 | 883. |
| | B | 57.8 | 896. |
| | C | 60.2 | 1007. |
| LOCATION IN HOLE: | | | |
| | SIDE-FACE (T) | 64.3 | 1320. |
| | FLUTE-END (B) | 52.2 | 758. |
| | HOLE FLOOR (F) | 59.5 | 707. |
| ANODE END: | | | |
| | CENTER OF ANODE @ MID-HEIGHT | 67.4 | 587. |
| | INSIDE SHOULDER OF SLOT | 62.0 | 609. |
| | ABOVE SLOT | 63.5 | 644. |
| | CENTER OF ANODE @ BOTTOM | 76.5 | 1258. |
| | EDGE @ MID-HEIGHT | 76.9 | 802. |
| | OUTSIDE SHOULDER OF SLOT | 64.2 | 678. |
| POSITION ON SIDE OF ANODE: | | | |
| | A | 75.2 | 824. |
| | B | 69.4 | 892. |
| | C | 69.2 | 765. |
| | D | 72.4 | 747. |
| | E | 71.7 | 928. |
| | F | 78.9 | 1003. |
| ORIENTATION: | | | |
| | VERTICAL | 70.6 | 858. |
| | LONGITUDINAL | 74.4 | 856. |

FIG.10

| COEFFICIENT OF VARIATION FOR DIFFERENT LOCATIONS: | | |
|---|---|---|
| LOCATION: | BAKED | GREEN |
| STUB-HOLE | 0.067 | 0.27 |
| ANODE END/SLOTS | 0.097 | 0.33 |
| ANODE SIDE | 0.051 | 0.12 |

| FIG. 17A |
|---|
| FIG. 17B |

METHODS FOR DETERMINING GREEN ELECTRODE ELECTRICAL RESISTIVITY AND METHODS FOR MAKING ELECTRODES

CROSS REFERENCE TO RELATED APPLICATIONS

This patent application is a non-provisional of and claims priority to U.S. Patent Application No. 61/747,742 filed Dec. 31, 2012, and U.S. Patent Application No. 61/783,933 filed Mar. 14, 2013, both of which are incorporated herein by reference in their entirety.

FIELD OF THE INVENTION

The instant disclosure is directed towards an apparatus and methods of using the apparatus in electrode (anode) processing. More specifically, the instant disclosure is directed towards an apparatus for measuring the electrical resistivity of a green form of an electrode (e.g. anode) and utilizing the green form electrical resistivity to adjust (if necessary) the processing parameters of the electrode (e.g. mixing parameters, anode composition/pitch content, forming parameters, and combinations thereof).

BACKGROUND

Electrolytic aluminum production efficiency is influenced by anode quality. Testing is conventionally done on baked anodes and is completed on a small number of the total anodes produced. Further, testing is often completed long after the anodes have shipped to a smelter or are being used in a smelter.

SUMMARY OF THE INVENTION

Aluminum production efficiency is influenced by anode quality. In some embodiments, microstructure variations within anodes (baked anodes and/or green anodes) are reflected in the electrical conductivity of the anodes. The instant disclosure is directed towards an apparatus configured to measure the electrical resistivity in electrodes (e.g. green anodes), in a non-destructive method in order to characterize anodes (e.g. quality of green anodes) and/or quantify the impact of the anode production process/process parameters on the anode. In some embodiments, properties like density and electrical resistivity of the anode (e.g. carbon block) correlate to the underlying microstructure of the anode. In some embodiments, variations in electrical resistivity within an anode relates to processing parameters including, but not limited to: forming/manufacturing steps, materials, anode composition, or design. In some embodiments, the apparatus, system, and corresponding methods are configured to provide measurements of electrical resistivity in anodes which are effective at measuring microstructure variations, including for example, anisotropic behaviors, the effect of molded forms, and/or the influence of edge areas.

In some embodiments, the apparatus, system, and methods are configured to provide electrical resistivity measurements which cover most of the anode (e.g. green anode) volume or surface area (e.g. anode map).

In one aspect of the instant disclosure, a method is provided. The method comprises: determining a measured voltage drop across a green anode surface via an electrical resistivity device positioned to contact the green anode surface; correlating a measured electrical resistivity from the voltage drop; comparing the measured electrical resistivity to a target electrical resistivity; and adjusting (if necessary), based on the comparing step, at least one of anode processing parameters. In some embodiments, based on the comparing step, no adjustment is made (i.e. the measured value is within or at the target value).

In one embodiment, the adjusting step is selected from the group consisting of: changing a pitch to coke ratio; changing a mixing temperature; changing a mixing time; changing a mixing RPM; or changing an amount of agitation via mixing; changing the anode granulometry; changing one or more of the forming parameters; and combinations thereof.

In one embodiment, the adjusting a forming parameter comprises changing: a temperature; a cycle time; a pressure applied; a dwell time for pressure application, a vibration frequency, a vibration amplitude, a vacuum, a bellows pressure, and combinations thereof.

In one embodiment, the correlating, comparing, and adjusting step are completed via a specifically programmed computer.

In one embodiment, the method further comprises indicating a quality of the green anode (e.g. high, medium, low) via the measured electrical resistivity. As a non-limiting example, using the data obtained with reference to FIG. 16, the anodes which have electrical resistivity measurements that are the statistical outliers (e.g. outside the standard deviation, or 95% confidence levels) having high measured values of electrical resistivity (as compared to the statistical mean values for that group) for a group of anodes manufactured at a particular pitch wt. % are low quality. In this embodiment, values around the mean value for a group of green anodes having a particular pitch content (wt. %) are medium, and values below the mean value for a group of green anodes having a particular pitch content are high. In one embodiment, when a plurality of electrical resistivity values are taken on the green anode, the values are compared to average values for each measurement for similarly manufactured green anodes (e.g. having a same wt. % of pitch) and the quality is quantified via comparisons of the "anode map" to the mean values or other statistical metrics.

In one embodiment, the method further comprises: indicating a green anode quality via a specifically designed computer.

In another aspect of the instant disclosure, a method is provided, comprising: mixing a first composition comprising: an amount of coke and an amount of pitch; forming a green anode in a mold having the first composition therein; positioning an electrical resistivity device about the green anode to define at least one electrical current path, wherein the electrical resistivity device comprises: at least two probes adapted to contact a portion of the anode surface of the anode and configured to measure the voltage drop across the current path; and at least one electrical current source positioned in a spaced relation from the at least two probes, wherein the current source is adapted to contact another portion of the surface, wherein the current source is configured to transmit an electrical current from a current inlet through the anode body to the current outlet; determining a measured voltage drop across the green anode surface via the electrical resistivity device; correlating an electrical resistivity from the current and the voltage drop across the at least one electrical current path; comparing the measured electrical resistivity to a target electrical resistivity; and adjusting, based on the comparing step, at least one of the mixing step or the forming step.

In one embodiment, determining comprises: directing a current output of not greater than 5 amps from the current inlet to the current outlet.

In one embodiment, the forming step comprises: pouring the first composition into a mold, and pressing the first composition in the mold to form a green anode.

In one embodiment, the pressing step comprises vibrocompaction.

In yet another aspect, a method is provided, comprising: mixing a first composition comprising: coke and pitch, forming a green anode in a mold having the first composition therein; positioning a plurality of electrical resistivity devices about the green anode, wherein each electrical resistivity device is configured to contact an anode surface to define an electrical current path per each electrical resistivity device, wherein each electrical resistivity device comprises: at least two probes adapted to contact a portion of the anode surface of the anode and configured to measure the voltage drop across the current path; and at least one electrical current source positioned in a spaced relation from the at least two probes, wherein the current source is adapted to contact another portion of the surface, wherein the current source is configured to transmit an electrical current from a current inlet through the anode body to the current outlet; determining a measured voltage drop across the anode surface for each electrical resistivity device; correlating an electrical resistivity from the current and the voltage drop across the at least one electrical current path for each electrical resistivity device; providing an anode map indicative of electrical resistivity which is compiled from the measured electrical resistivity measurements for various portions on the green anode.

In one embodiment, positioning comprises: positioning at least four electrical resistivity devices onto an anode surface to obtain electrical resistivity measurements in a top, bottom, horizontal, and vertical direction along the anode surface.

In one embodiment, positioning further comprises: positioning at least one of the plurality of electrical resistivity devices to provide an electrical resistivity measurement over two sides of the green anode via positioning one of the electrical probes and the current inlet orthogonally from the other electrical probe and the current outlet.

In one embodiment, the positioning step is across a corner of the green anode.

In one embodiment, the positioning step is across two opposing sides of the green anode.

In one embodiment, the positioning, correlating, determining, and providing steps are completed on green anodes in an anode production line.

In one embodiment, the determining further comprises an electrical control system, which is configured to activate each of the plurality of electrical resistivity devices sequentially to obtain electrical resistivity measurements for each electrical resistivity devices on the green anode.

In one embodiment, the positioning, correlating, determining, and providing steps are performed via a specifically programmed computer configured to be in electrical communication with the plurality of electrical resistivity devices.

In one embodiment, the plurality of measurements are completed sequentially. In one embodiment, the plurality of measurements are completed simultaneously by using alternating current at different frequencies (wherein each electrical resistivity devices comprises a current inlet having a separate AC frequency which is different from each other electrical resistivity device's current frequency). In this embodiment, the simultaneous measurements are filtered electronically (via one or a plurality of electrical filters (e.g. one for each electrical resistivity device) to provide each measured voltage drop (specific to each anode portion), which is correlated to an electrical resistivity (specific to each anode portion). In some embodiment, the simultaneous measurements are completed and tracked with a specifically programmed computer (e.g. which is also in electrical communication with the electrical filter).

In one embodiment, the method comprises: indicating a green anode quality via the specifically designed computer.

In one aspect of the instant disclosure, a method is provided, comprising: determining a measured voltage drop across a green anode surface via an electrical resistivity device positioned to contact the anode surface; correlating a measured electrical resistivity from the voltage drop; comparing the measured electrical resistivity to a target electrical resistivity; and adjusting, based on the comparing step, at least one of anode processing parameters.

In another aspect of the instant disclosure, a method is provided, comprising: mixing a first composition comprising: coke and pitch (e.g. optionally, anode butts); forming a green anode in a mold having the first composition therein; positioning an electrical resistivity device about the green anode to define at least one electrical current path, wherein the electrical resistivity device comprises: at least two probes adapted to contact a portion the anode surface of the anode and configured to measure the voltage drop across the current path; and at least one electrical current source positioned in a spaced relation from the at least two probes, wherein the current source is adapted to contact another portion of the surface, wherein the current source is configured to transmit an electrical current from a current inlet through the anode body to the current outlet (AC or DC); determining a measured voltage drop across the anode surface; correlating an electrical resistivity from the current and the voltage drop (e.g. depends on geometry of anode and probe) across the at least one electrical current path; comparing the measured electrical resistivity to a target electrical resistivity; and adjusting, based on the comparing step, at least one of the mixing step or the forming step.

In some embodiments, the electrical resistivity device has a current output of between 1 Amp and 100 Amps. In some embodiments, the current source provides: at least about 1 A; at least about 5 A; at least about 10 A; at least about 15 A; at least about 20 A; at least about 25 A; at least about 30 A; at least about 35 A; at least about 40 A; at least about 45 Å; at least about 50 A; at least about 55 Å; at least about 60 A; at least about 65 A; at least about 70 A; at least about 75 A; at least about 80 A; at least about 85 A; at least about 90 A; at least about 95 A; or at least about 100 A of current. In some embodiments the current source provides over 100 A of current.

In some embodiments, the current source provides: at least about 0.25 A; at least about 0.5 A; at least about 0.75 A; at least about 1 A; at least about 1.25 A; at least about 1.5 A; at least about 1.75 A; at least about 2.0 A; at least about 2.25 A; at least about 2.5 A; at least about 2.75 A; at least about 3 Å; at least about 3.25 A; at least about 3.5 A; at least about 3.75 A; at least about 4 A; at least about 4.25 A; at least about 4.5 A; at least about 4.75 A; or at least about 5 A of current.

In some embodiments, the electrical resistivity device has a current output of between 1 Amp and 100 Amps. In one embodiment, the current source provides: not greater than about 1 A; not greater than about 5 A; not greater than about 10 A; not greater than about 15 A; not greater than about 20 A; not greater than about 25 A; not greater than about 30 A; not greater than about 35 A; not greater than about 40 A; not greater than about 45 Å; not greater than about 50 A; not greater than about 55 Å; not greater than about 60 A; not greater than about 65 A; not greater than about 70 A; not greater than about 75 A; not greater than about 80 A; not greater than about 85 A; not greater than about 90 A; not greater than about 95 A; or not greater than about 100 A.

In some embodiments, the current source provides: not greater than about 0.25 A; not greater than about 0.5 A; not greater than about 0.75 A; not greater than about 1 A; not greater than about 1.25 A; not greater than about 1.5 A; not greater than about 1.75 A; not greater than about 2.0 A; not greater than about 2.25 A; not greater than about 2.5 A; not greater than about 2.75 A; not greater than about 3 A; not greater than about 3.25 A; not greater than about 3.5 A; not greater than about 3.75 A; not greater than about 4 A; not greater than about 4.25 A; not greater than about 4.5 A; not greater than about 4.75 A; or not greater than about 5 A of current.

In still another aspect of the instant disclosure, a method is provided, comprising: mixing a first composition comprising: coke and pitch forming a green anode in a mold having the first composition therein; positioning an electrical resistivity device about the green anode to define at least one electrical current path, wherein the electrical resistivity device comprises at least two probes adapted to contact a portion the anode surface of the anode and configured to measure the voltage drop across the current path; and at least one electrical current source positioned in a spaced relation from the at least two probe, wherein the current source is adapted to contact another portion of the surface, wherein the current source is configured to transmit an electrical current from a current inlet through the anode body to the current outlet (AC or DC); determining a measured voltage drop across the anode surface; correlating an electrical resistivity from the current and the voltage drop (depends on geometry of anode and probe) across the at least one electrical current path; comparing the measured electrical resistivity to a target electrical resistivity; and adjusting, based on the comparing step, at least one of the mixing step or the forming step.

In some embodiments, the forming step comprises pouring the anode into a mold, pressing, and/or compaction (e.g. vibrocompaction). In some embodiments, the forming step comprises isostatic pressing.

In some embodiment, the method comprises baking the formed anode.

In some embodiments, the forming step comprising compacting the anode mixture via a vibrocompactor. In some embodiments, the vibrocompactor vibrates to shake/compact the anode mixture in a mold.

In some embodiments, the forming step (e.g. pressing and/or vibrocompacting) comprises at least one of: a forming temperature; a cycle time; a pressure applied; a dwell time for pressure application (e.g. time of pressure application), vibration frequency, vibration amplitude, vacuum, bellows pressure, and combinations thereof.

In yet another aspect of the instant disclosure, a method is provided, comprising: contacting a plurality of probes to a surface of a green anode; directing current across the anode body from a first position to a second position; and determining an electrical resistivity across a distance on a surface of the green anode (e.g. between the current input and outlet).

In still yet another aspect of the instant disclosure, an apparatus is provided, comprising: at least one electrical resistivity device, comprising: at least two current probes, configured to contact a surface of a green anode and direct current across the anode surface; and at least two electrical probes, placed at a distance from each other and between the current probes, wherein the electrical probes are configured to measure a voltage drop across the distance of the anode surface; a power source (e.g. a current source—AC or DC), configured to supply current to the electrical resistivity device; and at least one frame, configured to fit alongside of the anode surface, wherein the frame includes a plurality of holes along a length thereof at a predetermined distance from one another, wherein the holes are configured to accept and retain at least one of: the current probes and the electrical probes.

In one embodiment, measurements are taken with the electrical resistivity device in a sequential manner, wherein the device is configured to first direct a current from the inlet to the outlet, then measure the voltage drop with the electrical probes.

In some embodiments, the measurements with the electrical resistivity device are taken in a simultaneous manner, where the current is directed across the anode surface while and/or at the same time as the voltage drop is measured by the electrical probes.

In some embodiments, the frame comprises an electrical insulation material and/or a thermal insulation material. In some embodiments, the frame is configured to insulate the probes (e.g. current and/or electrical probes) from each other.

In some embodiments, the frame comprises at least one anchoring device, wherein the anchoring device is configured to retain at least one probe in at least one hole and is configured such that the probe applies a threshold pressure (e.g. contact pressure) to the surface of the anode.

In some embodiments, the apparatus comprises: at least 2 electrical resistivity devices; at least 3 electrical resistivity devices; at least 4 electrical resistivity devices, at least 8 electrical resistivity devices, at least 10 electrical resistivity devices, at least 15 electrical resistivity devices, or more.

In some embodiments, the apparatus comprises a plurality of frames, where the frames are configured and/or positioned orthogonally to one another. In this embodiment, electrical resistivity measurements are taken over a corner of an anode, or on two sides (e.g. a top and a bottom, a bottom and a side, and side and a top, or the like).

In some embodiments, the apparatus is automated such that the positioning of the frame(s) and the electrical resistivity device(s) is automatic around at least some (or all) anodes in an anode production line.

In some embodiments, the apparatus comprises an electrical control system, which is configured to activate each electrical resistivity device sequentially (e.g. into separate measurements).

In some embodiments, the apparatus comprises a computer in electrical communication with the electrical resistivity device and configured to receive the voltage drop across the anode surface and correlate an electrical resistivity measurement(s) and/or current measurement (e.g. simultaneous with electrical resistivity measurement), indicative of the green anode quality.

In some embodiments, the computer is configured to use a conversion factor (sometimes called a calibration factor) for electrical resistivity of the green anode. In some embodiments, the conversion factor is based upon at least one of the following variables, including but not limited to: the length of the path along the anode surface; the position of the path on the anode (e.g. geography on the anode, corner vs. middle) the current, the voltage drop, the anode material (e.g. carbon), the anode composition (e.g. ratio of coke to pitch, coke granulometry, and spent anode content); and combinations thereof.

In some embodiments, multiple electrical resistivity measurements are compiled via the computer to provide an anode map. In some embodiments, the anode map indicates the anode density and/or structure, and is indicative of cracks or microstructure deviations.

As used herein, "electrode" means: a conductor (not necessarily metallic) through which a current enters or leaves a nonmetallic medium (e.g. a carbon anode, a green anode, or an electrolytic cell.) In some embodiments, the electrode is an anode. In some embodiments, the electrode is a cathode.

As used herein, "anode" means: an article intended for use as a positively charged electrode in an electrolytic cell (or pot). When used herein, unless otherwise denoted, anode refers to green anode. In some embodiments, the anode comprises carbon and is consumed by oxygen during electrolysis of non-ferrous metals (e.g. aluminum). In some embodiments, the anode comprises an inert composition which emits oxygen during electrolysis and which does not substantially degrade/is not consumed to the extent that a carbon anode is during the electrolysis process. In various embodiments of the instant disclosure, the aspects of the apparatus, systems, and methods are utilizable with various green anode compositions and/or green cathode compositions (TiB2, carbon, ceramics, hybrid ceramic/carbon forms). In some embodiments, anode refers to a green anode. In some embodiments, anode refers to a baked anode (i.e. final monolithic block of carbon, after the green anode is baked).

As used herein, "green anode" means: an anode formed by mixing and forming (e.g. by compressing and/or shaping) the anode composition (e.g. carbon composition having coke and pitch or an inert anode composition of cermet, ceramic or metallic composition) prior to baking. In some embodiments, a green anode is a formed anode (in the final anode form) that is not yet baked. In some embodiments, the final baking step (e.g. to make a green anode into a baked anode) is performed to remove volatile components from the anode (e.g. from the pitch) and/or decrease the electrical resistivity of the anode. In some embodiments, the final baking step transforms the green anode into a baked anode (e.g. a monolithic block of coke, monolithic block of ceramic, cermet, or metallic composition).

As used herein, "cathode" means: the negative electrode in an electrolytic cell. In one embodiment, the cathode is a carbon cathode. In one embodiment, the cathode is a ceramic cathode (e.g. titanium diboride). In one embodiment, the cathode is a hybrid (e.g. carbon and ceramic materials).

As used herein, "top" means: the highest point of something.

As used herein, "stub hole" means: a hole for the anode stub. In some embodiments, the stub hole is in the top of the anode.

As used herein, "anode stub" means: the metal pin which makes electrical contact with the anode carbon mass (usually fixed with an iron casting) via the stub hole.

As used herein, "bottom" means: the lowest point of something. In some embodiments, the anode bottom is the first portion of the anode to touch the electrolytic bath of an aluminum electrolysis cell.

As used herein, "side" means: a surface forming the outside of something.

As used herein, "mixing" means: to combine different components through blending and/or kneading. In one embodiment, coke and pitch are mixed to form an electrode composition (e.g. anode or cathode composition). In one embodiment, compounds are mixed to form an green electrode composition having a cermet, ceramic, or metallic composition.

As used herein, "coke" means: an electrical conductor in the green anode. In some embodiments, the coke is the carbonaceous residue made from residual fuel oils produced in petroleum refining. Some non-limiting examples of coke include: pet coke, pitch coke, coke from coal, and combinations thereof.

As used herein, "pitch" means: an electrical insulator in the green anode. In some embodiments, the pitch is a heat-treated tar originating from the coking of coal. Some non-limiting examples of pitch include coal tar pitch and petroleum pitch.

As used herein, "composition" means: a material formed of two or more substances. As one non-limiting example, the anode composition (sometimes called a "paste") refers to a material formed from pitch and coke (e.g. with optional additives and/or binders). In some embodiments, variations in the composition (e.g. the pitch to coke ratio) allows for variations in the green anode (and final baked anode) properties and characteristics.

In some embodiments, increased coke in the coke:pitch ratio allows for improved packing of the composition (e.g. higher density, and lower electrical resistivity of the resulting anode). In some embodiments, the green anode electrical resistivity changes with the amount of pitch used (coke:pitch ratio) in the paste or anode composition.

As used herein, "forming" means: to make an object. Some non-limiting examples of forming include pressing and vibrocompacting. In one embodiment, the electrode composition undergoes a forming step to produce a green form/electrode. In one embodiment, the composition is directed into a mold which undergoes a compacting via a vibrocompactor.

As used herein, "pressing" means: to act upon with applied weight or force. In some embodiments, pressing conforms the composition to the shape and size of the green anode (e.g. via a mold).

As used herein, a "vibrocompactor" means: a compactor apparatus that compacts via a vibrating bench that vibrates the materials together (e.g. in some embodiments, with the assistance of a pressing mass on the top of the anode paste).

As used herein, "vibrating bench" means: a bench that vibrates.

As used herein, "baking" means to cook (e.g. harden) by application of heat (e.g. applied in an oven).

As used herein, "electrical resistivity device" means: a device for measuring electrical resistivity. In one embodiment, an electrical resistivity device includes a four point probe (e.g. two voltage probes, two current probes). In one embodiment, an electrical resistivity device comprises probes for transmitting and receiving current and measuring voltage drop across the material/surface that is electrically connected to the probes.

In one embodiment, an electrical resistivity device is used on a green electrode to measure the electrical resistivity of the green form. In one embodiment, an electrical resistivity device is repositioned within holes of a frame to obtain multiple measurements with one electrical resistivity device having different probe placement around/about the green electrode surface. In one embodiment, multiple/a plurality of electrical resistivity devices are used on a green electrode (i.e. at various positions) to measure the electrical resistivity of the green form in multiple positions (e.g. in order to correlate inhomogeneity of the electrode).

As used herein, "voltage drop" means: a decrease in voltage along a conductor through which current is flowing. In some embodiments, voltage drops across green electrodes are measured and quantified in accordance with various aspects of the instant disclosure.

As used herein, "electrical resistivity" (sometimes called resistivity or specific electrical resistance) means: a quantification of how strongly a given material opposes the flow of electric current. Electrical resistivity is typically expressed as Ohm*meter ($\Omega$*m).

As used herein, "target electrical resistivity" means: an electrical resistivity which is configured for and attributable to a processing parameter indicative of a characteristic of a green form (e.g. electrode, anode, or cathode).

In some embodiments, the target electrical resistivity is a minimum value for a given variable (processing parameter or electrode characteristic). In some embodiments, the target electrical resistivity is a maximum value for a given processing parameter (or characteristic). In some embodiments, the target electrical resistivity is below a certain threshold value for a given processing parameter (or characteristic). In some embodiments, the target electrical resistivity is above a certain threshold value for a given processing parameter (or characteristic). In some embodiments, the target electrical resistivity is within a range for a given processing parameter (or characteristic). In some embodiments, the target electrical resistivity is outside of a range for a given processing parameter (or characteristic). In some embodiments, the electrical resistivity may be a function of a processing parameter (or characteristic), and the target electrical resistivity is determined via observing the trend line/functional relationship of the resistivity with the parameter or characteristic of the electrode.

As used herein, "probe" means: an object used for making a connection (e.g. mechanical or electrical connection).

As used herein, "voltmeter" means: a meter for measuring voltage.

As used herein, "current source" means a source for electrical current. In some embodiments, the current source is AC. In some embodiments, the current source is DC.

As used herein, "computer" means: an electronic device designed to accept data, perform operations (e.g. mathematical and logical operations) and provide a feedback of the results (e.g. through a display to an operator).

As used herein, "display" means: a device which shows information. As a non-limiting example, the electrical resistivity device is configured with a computer which has a display to provide information (e.g. electrical resistivity, referred change in anode processing parameters) to an operator or system.

As used herein, "density" means: the mass per unit volume of an object. As a non-limiting example, density refers to a state or quality of compactness in an anode (e.g. green anode).

As used herein, "crack" means: a break or discontinuous region in an object without the complete separation of the object into two or more parts. In one embodiment, the electrical resistivity device is configured to measure an electrical resistivity along the electrode and identify crack(s) in the electrode.

As used herein, "formation" means: the process of forming something. In one embodiment, the electrical resistivity device is configured to measure electrical resistivity across multiple locations on an anode (or across multiple anodes) in order to correlate trends in the anode production/processing parameters and equipment for the forming step that attribute to inhomogeneity of the green anode.

As used herein, "propagation" means: the act of transmitting something.

Without being bound by a particular mechanism or theory, it is believed that a "low" resistivity indicates a material that readily allows the movement of electrical charge. Along the same lines, a "high" resistivity is believed to indicate a material that does not readily allow for the movement of electrical charge.

In some embodiments, for anodes used in electrolysis, a lower electrical resistivity in the anode means that the anode material does not strongly oppose electric current so the current is directed into or out of the cell with little resistance, resulting in more efficient cell operation. For example an electrode with a low resistivity is a better conductor of electrical charge than an electrode with a high resistivity, so in the electrolytic production of non-ferrous metal, better conductors provide for a more efficient system (e.g. lower voltage drop of the system).

As used herein, "current density" means: the amount of current passing through a given area of a material (e.g. an anode). Current density is typically expressed as amperes per square centimeter ($A/cm^2$).

As used herein, "current efficiency" means: the ratio of the quantity of metal produced in the cell by the current passing through compared to that theoretically expected from Faraday's Law, but expressed as a percentage.

As used herein, "current path" means: a path that current follows through an object or material.

As used herein, "aberration" means: an inconsistency in a material which results in the departure from the normal course. In some embodiments, cracks or microstructure variations in electrodes are aberrations which result in deviations from the electrical current flow as it travels through the anode or cathode.

As used herein, "homogenous" means: having a common property throughout (e.g. of a uniform nature).

As used herein, "heterogeneous" means: composed of parts of different kinds; having widely dissimilar elements or constituents. In some embodiments (e.g. at small length scales about the size of the coke particles), the anodes are heterogeneous, being made of coke aggregate and either pitch or pitch coke (i.e. inherent in the anode composition). In some embodiments (e.g. at longer length scales) the anodes are heterogeneous with respect to the anode average resistivity (or other property) in a region of a certain size, which varies from place to place within the anode.) In one embodiment, heterogeneity (sometimes called inhomogeneity) is reduced, prevented, and/or eliminated in the green electrode by aspects of the instant disclosure.

Reference will now be made in detail to the accompanying drawings, which at least assist in illustrating various pertinent embodiments of the present invention.

BRIEF DESCRIPTION OF THE DRAWINGS

FIG. 10 is a table depicting baked vs. green anode comparisons of electrical resistivity measurements at different locations along the anodes.

These and other aspects, advantages, and novel features of the instant disclosure are set forth in part in the description that follows and will become apparent to those skilled in the art upon examination of the following description and figures, or may be learned by practicing the invention.

DETAILED DESCRIPTION

As the anode is the interface between the energy source and the reaction cell, the energy consumed by passing the electrical current through the anode block is basically a loss, as it does not contribute to the reduction of the alumina in the electrolysis cell. In one embodiment, the apparatus, system, and methods of the instant disclosure are directed towards utilizing an electrical resistivity device on a green form of an electrode in order to (1) determine the quality of the electrode (e.g. quality of high, medium, low, or pass/no pass; identify underlying inhomogeneities/inconsistencies in the electrode structure) and/or (2) impact the processing parameters for electrode production (e.g. composition, mixing parameters, forming parameters, and possible downstream baking parameters).

Without being bound to a particular mechanism or theory, it is believed that the green electrodes (prebaked carbon anodes or cathodes) obey Ohm's law; thus, a lower intrinsic electrical resistivity of the carbon in the anode block will result in an overall lower electrical resistance of the anode. Through one or more of the aspects of the instant disclosure, measurements of the electrical resistivity of the green anodes are made, which provides feedback as to whether there are any internal inconsistencies (e.g. inhomogeneity, cracks, voids, inclusions, inferior degree of coke packing (e.g. lower packing density)) and also provide feedback as to the electrical resistivity of the resulting (baked) anode.

In one embodiment, an electrical resistivity device/apparatus is used to measure green anode electrical resistivity and adjust manufacturing parameters in line in order to produce improved anodes (e.g. increased homogeneity). In some embodiments, one or more of the aspects of the instant disclosure are used to determine the optimum green anode electrical resistivity which corresponds to the highest baked anode density and/or lowest baked anode electrical resistivity. One or more embodiments of the instant disclosure provide an effective way to maintain process control of green anode manufacturing and resulting quality control of the final baked anodes.

Example 1

Electrical Resistivity Device & General Methodology

Figure 1:
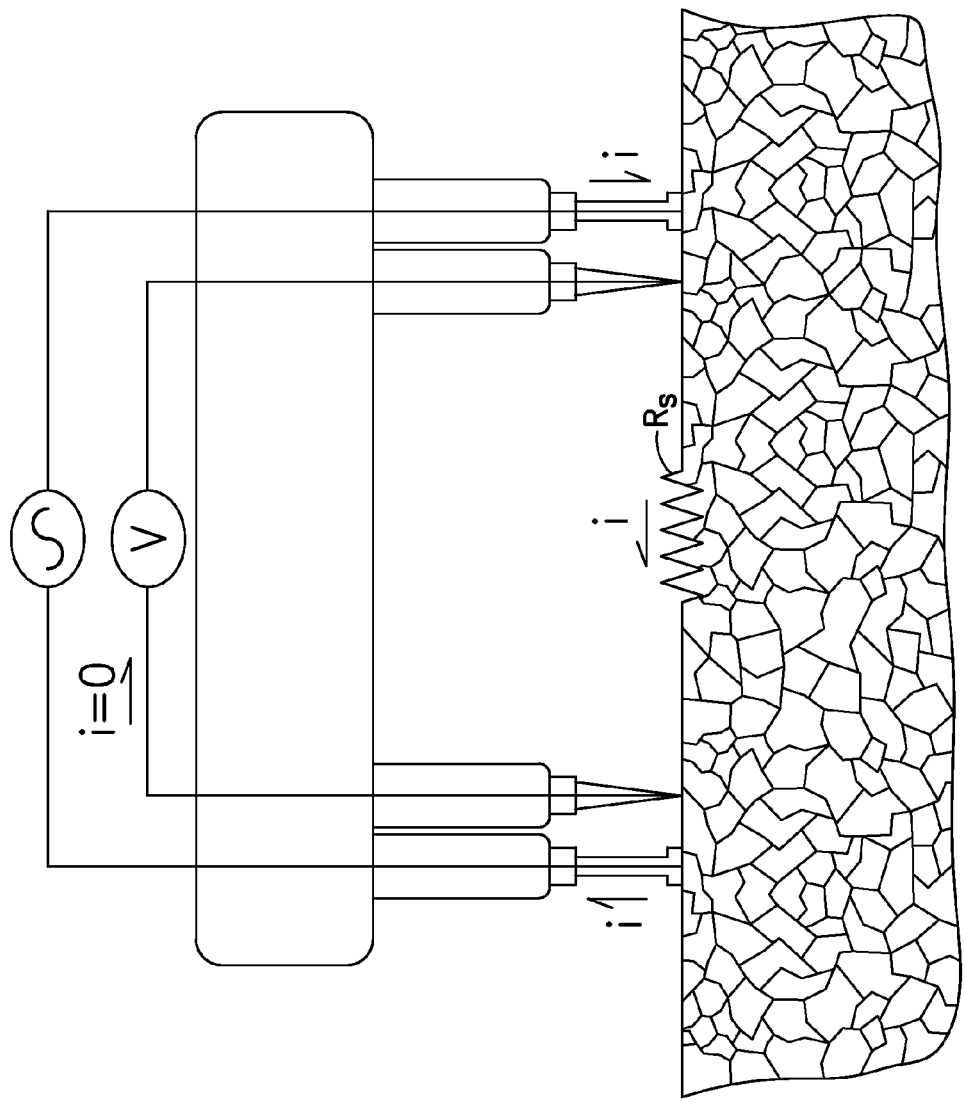
FIG. 1 depicts a drawing of an electrical resistivity device (e.g. a four point probe) used in accordance with the instant disclosure, illustrating the equivalent electrical circuit of the probe operation. The resistance (Rs) represents the equivalent volume resistance of the material.

Referring to FIG. 1, a device for measuring the electrical resistivity in a surface of an electrode (e.g. anode) is provided. FIG. 1 provides a drawing of the equivalent electrical circuit of the device in operation, where the resistance (Rs) represents the equivalent volume resistance of the material. As shown in FIG. 1, as the two outer current carrying probes are placed on the flat anode surface area, an electric potential distribution is generated within the electrode (e.g. carbon material) volume and surface. The electric current travels through the electrode body to complete the electrical circuit. The two outside tips (current probes) force current across the material from a source (AC or DC). Then, a reading of the voltage drop is measured by the two middle tips (electrical probes). Without being bound by a particular mechanism or theory, because the voltmeter resistance is much higher than the material resistance (e.g. carbon), it is assumed that all the current goes through the material meaning that the current (i) is the same all around the exterior wire and equal to zero across the voltmeter ($i_v=0$). For the experiments discussed under Example 1, the current probes are spaced apart from each other by 72.5 mm and the electrical probes are spaced apart from each other by 51.5 mm.

Without being bound to a particular mechanism or theory, there is a linear relationship between the voltage drop measured between the two inner probes and the electrical resistivity of the tested material. The later can be inferred from the voltage drop using a calibration factor, f. This factor in turn, will depend on other factors like the distance between the probes, geometry of the carbon block, shape of the probe's contact pads and relative position of the probes to the block geometry.

This relationship can be written as follows:

$$\rho = \frac{V}{I*f}$$

Where $\rho$ is the electrical resistivity, f is the above mentioned calibration factor, V is the voltage drop measured and I is the electric current applied.

For the same anode geometry and identical measurement location, the factor f used was the same for all the measurements, regardless of the presence of any internal flaws. Without being bound to any particular mechanism or theory, it is believed that for any internal discontinuity that may alter the length of the electric current path, or which may change the cross section of the volume travelled by the electric current, changing the electric potential distribution, the corresponding change in voltage drop will be interpreted as a change in the intrinsic electrical resistivity of the electrode material (e.g. carbon). Without being bound by a particular mechanism or theory, it is expected that changes that impact the electrical resistance of the block will be exposed by this measurement as an electrical resistivity change, without having the capability to discern whether the change is an intrinsic resistivity change, as it would be expected from a different level of graphitization of the carbon material, or is an internal discontinuity problem.

Electrical resistivity measurements were taken on both baked anodes and green anodes. In one embodiment, the green anode block is heterogeneous, composed of calcined coke, an electrical conductive material, and pitch, an electrical insulator. Without being bound to a particular mechanism or theory, the electrical conductivity of the green block, even if very poor, can reflect the quality and the number of the points of contact between the coke particles. Therefore, this measurement can detect the presence of cracks and micro- Referring to FIG. 2, H refers to the large horizontal instrument, V refers to the large vertical instrument, T refers to the small top instrument, and B refers to the small bottom instrument.

Figure 3A:
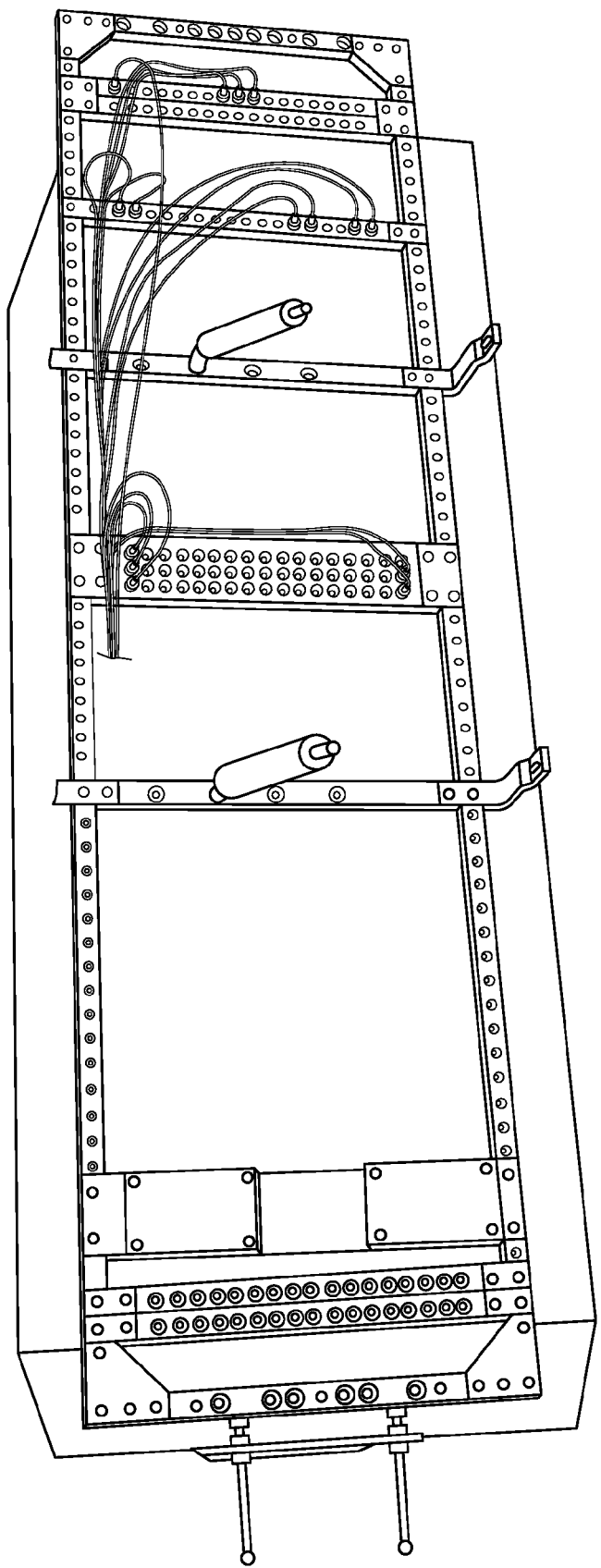
FIG. 3A depicts an electrical resistivity device (e.g. four point probe assembly) indexed on the flat anode surface.
Figure 3B:
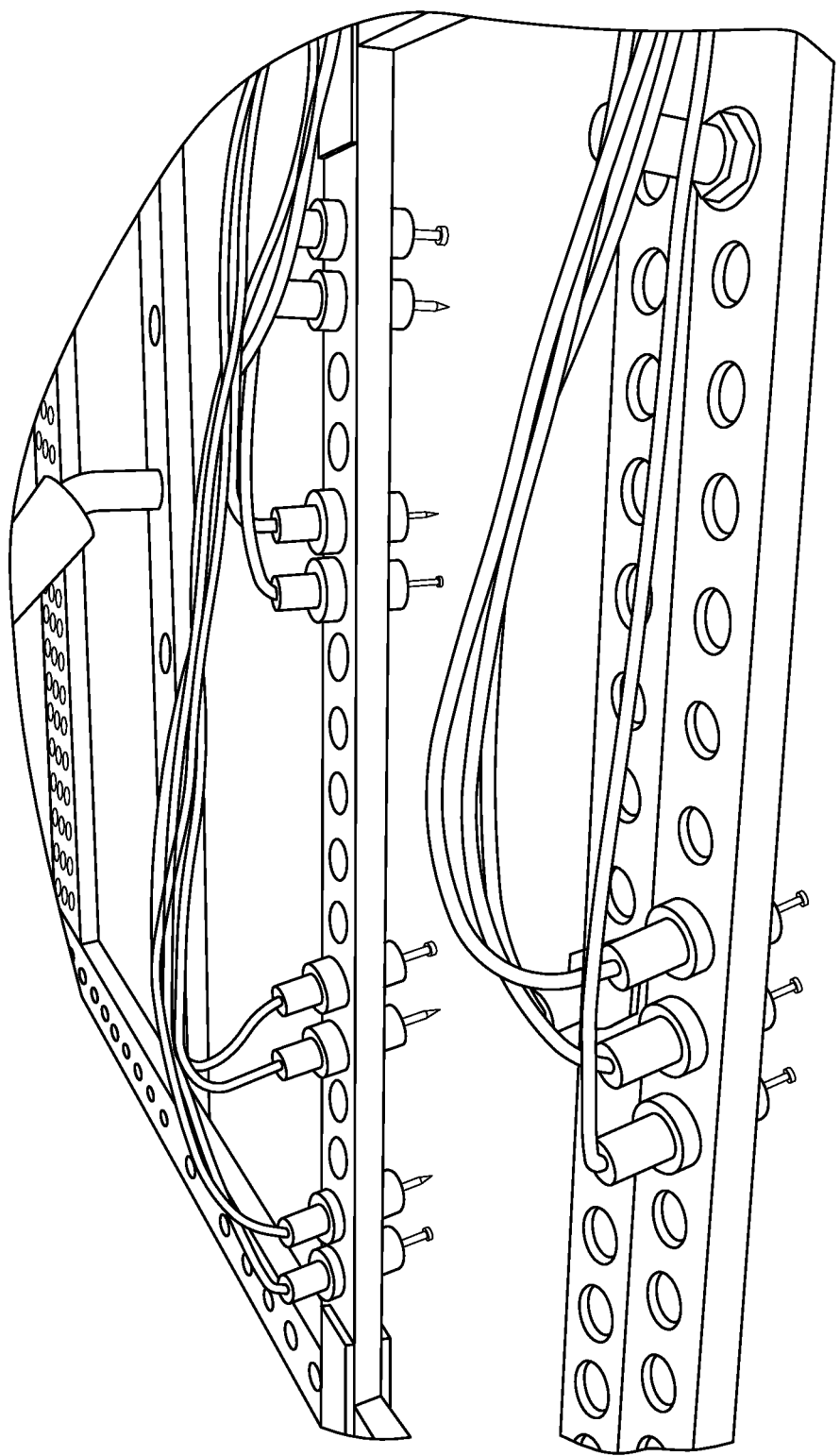
FIG. 3B depicts the perforated frame (which is configured to hold the probes at adjustable, preset distances) and some of the probes.

FIG. 3A depicts the four electrical resistivity devices held via the frame assembly over an anode. Referring to FIGS. 3A and 3B, the frame was perforated such that the respective probes' position/orientation was adjustable in one inch increments, such that even with adjustment, the probes maintained their horizontal or vertical orientation, respectively. FIG. 3A depicts the general assembly, while FIG. 3B is a close-up perspective side view the frame and some of the probes. The two larger instruments use separate DC power sources, capable of an output of 75 A. The smaller probes, share a DC power capable of an output of 20 A. Each power source has an individual on/off switch, allowing for the measurements to be taken successively, one instrument being active at a time.

Some of the factors used for the examples herein are presented in the table below.

TABLE I

Probe location, modeled voltage drop and calibration factor.

| Position | Probe-to-Shoulder (m) | Probe-to-Edge (m) | Probe-to-Shoulder (in) | Probe-to-Edge (in) | nVolts(5 A, 2000 S/m) | Calibration |
|---|---|---|---|---|---|---|
| Horizontal Probe: | | | | | | |
| 1 | 0.18415 | 0.04445 | 7.25 | 1.75 | 42.196 | 16878 |
| 2 | 0.0508 | 0.04445 | 2 | 1.75 | 44.984 | 17994 |
| 3 | 0.3556 | 0.04445 | 14 | 1.75 | 45.893 | 18357 |
| Vertical Probe | | | | | | |
| 1 | 0.01905 | 0.6858 | 0.75 | 27 | 19.71 | 7884 |
| 2 | 0.01905 | 1.0858 | 0.75 | 42.75 | 19.071 | 7628 |
| 3 | 0.0762 | 0.4572 | 3 | 18 | 19.162 | 7665 |
| 4 | 0.0762 | 0.2667 | 3 | 10.5 | 19.456 | 7782 |
| 5 | 0.0762 | 1.289 | 3 | 50.75 | 19.482 | 7793 |
| Small Probe - Top | | | | | | |
| 1 | 0.01905 | 0.22225 | 0.75 | 8.75 | 32.231 | 12892 |
| 2 | 0.01905 | 0.70485 | 0.75 | 27.75 | 32.252 | 12901 |
| 3 | 0.0762 | 1.1176 | 3 | 44 | 31.665 | 12666 |
| 4 | 0.0762 | 1.5367 | 3 | 60.5 | 50.017 | 20007 |
| 5 | 0.0762 | 0.01905 | 3 | 0.75 | 41.13 | 16452 |
| Small Probe - Bottom | | | | | | |
| 1 | 0.2286 | 0.22225 | 9 | 8.75 | 31.564 | 12626 |
| 2 | 0.2286 | 0.70485 | 9 | 27.75 | 31.462 | 12585 |
| 3 | 0.28575 | 1.1176 | 11.25 | 44 | 31.583 | 12633 |
| 4 | 0.28575 | 1.5367 | 11.25 | 60.5 | 49.945 | 19978 |
| 5 | 0.28575 | 0.01905 | 11.25 | 0.75 | 41.009 | 16404 | cracks, the degree of particles packing and the variation in pitch coating of the coke particles.

Example 2

Four Electrical Resistivity Devices (4-4 Point Probes)

Figure 2:
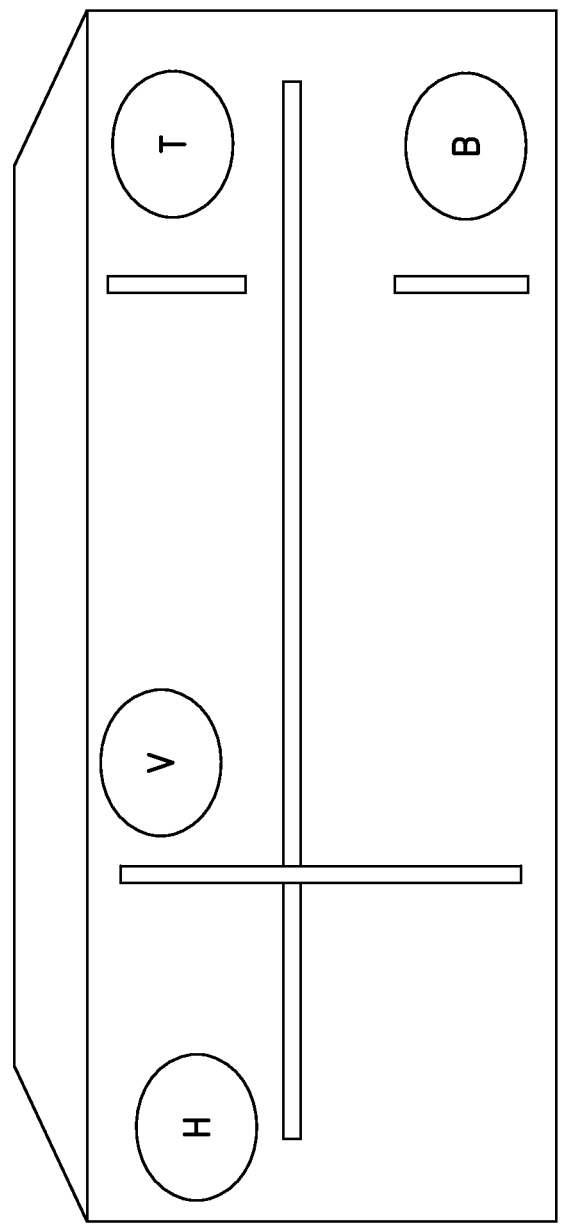
FIG. 2 is a schematic representation of the electrical resistivity device (comprising four-point probe assemblies) positioned on an electrode to obtain various measurements. "H" depicts the position of probe H, a large horizontal instrument. "V" depicts the position of probe V, a large vertical instrument. "T" depicts the position of probe T, a small top instrument. "B" depicts the position of probe B, a small bottom instrument.

An assembly of four devices was designed and held together rigidly by a larger frame. The frame offered the possibility to index the measurement's location relative to the anode surface via a plurality of holes at a predetermined distance along the frame body (i.e. which followed along the anode surface). A schematic representation of the location of the four instruments relative to an anode is depicted in FIG. 2.

Example 3

Measurements on Green Anodes and Baked Anodes

A study was completed on site at an anode manufacturing plant. Approximately 2400 measurements were taken, on full size anodes. One set of three measurements was taken on 11 baked anodes and on 11 green anodes, randomly picked from an anode inventory, which were considered to be representative.

The assembly of Example 2 was first indexed on the anode side and one measurement was taken. The second measurement was a repeat measurement, changing nothing. For the third measurement, the assembly was detached from the anode surface, and reset in the same location, using the indexing devices as guidance, making sure that the measurement is taken in the same location. At a later time, a new set of three measurements was taken on the same anodes. Again the frame was indexed to the anode surface such that the measurement would be taken in the same location as previously. The three measurements were taken as the ones in the first set, with one exception. After detaching the frame from the anode surface, for the third measurement, the frame was intentionally repositioned with a shift of approximately 0.5 inches from the previous location.

Figure 4:
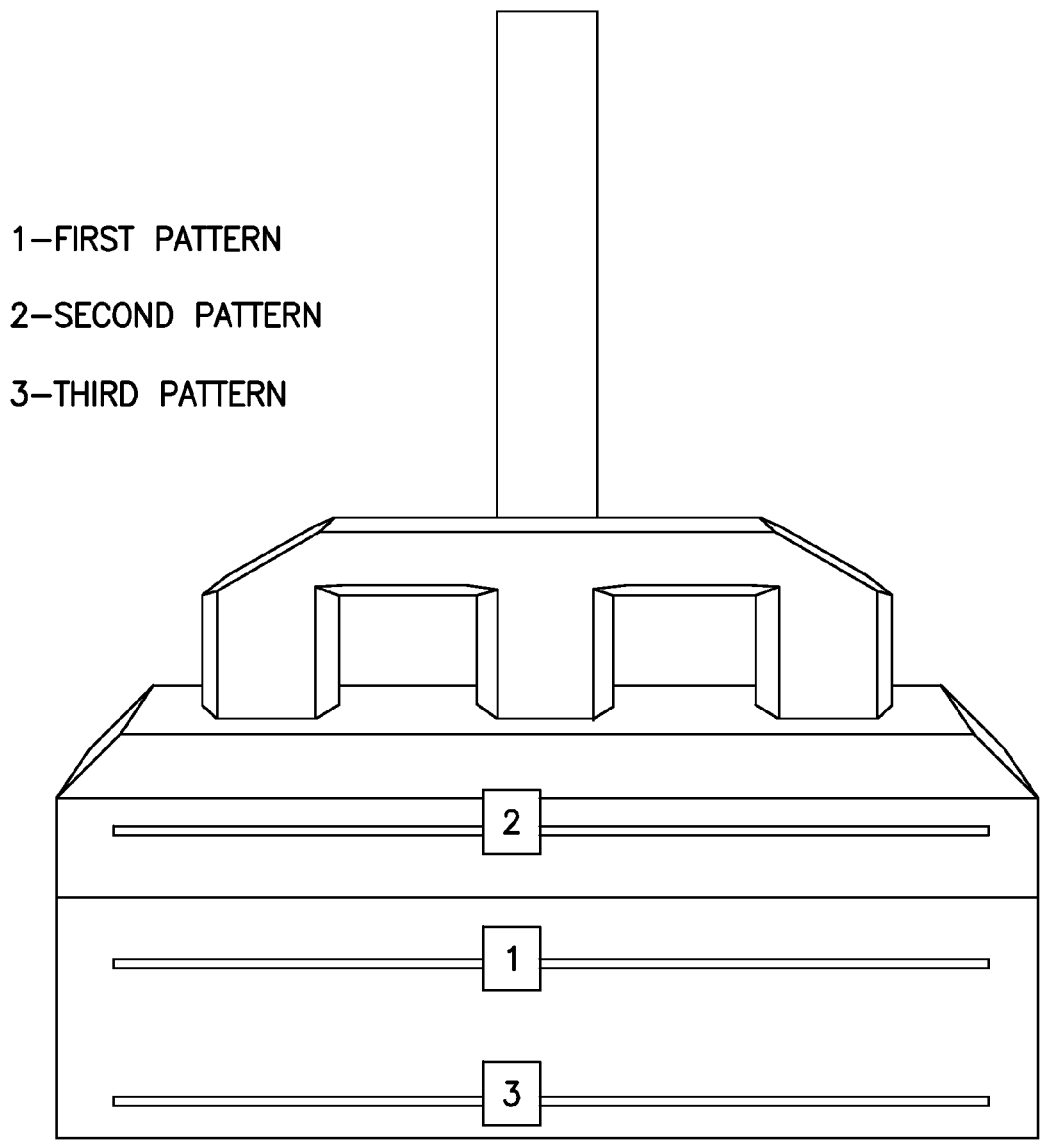
FIG. 4 depicts the horizontal instrument position (i.e. probe H), by pattern.
Figure 5:
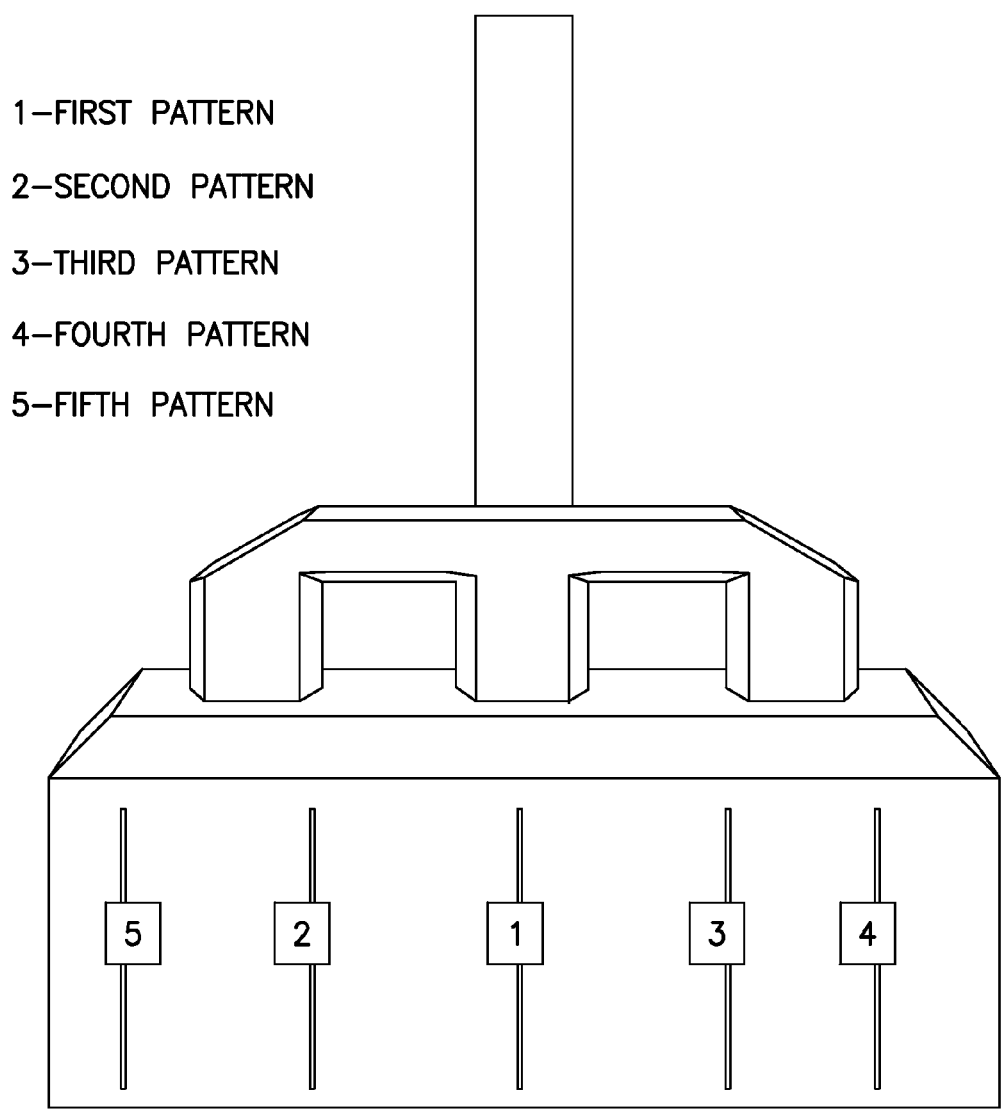
FIG. 5 depicts the vertical instrument position (i.e. probe V), by pattern.
Figure 6:
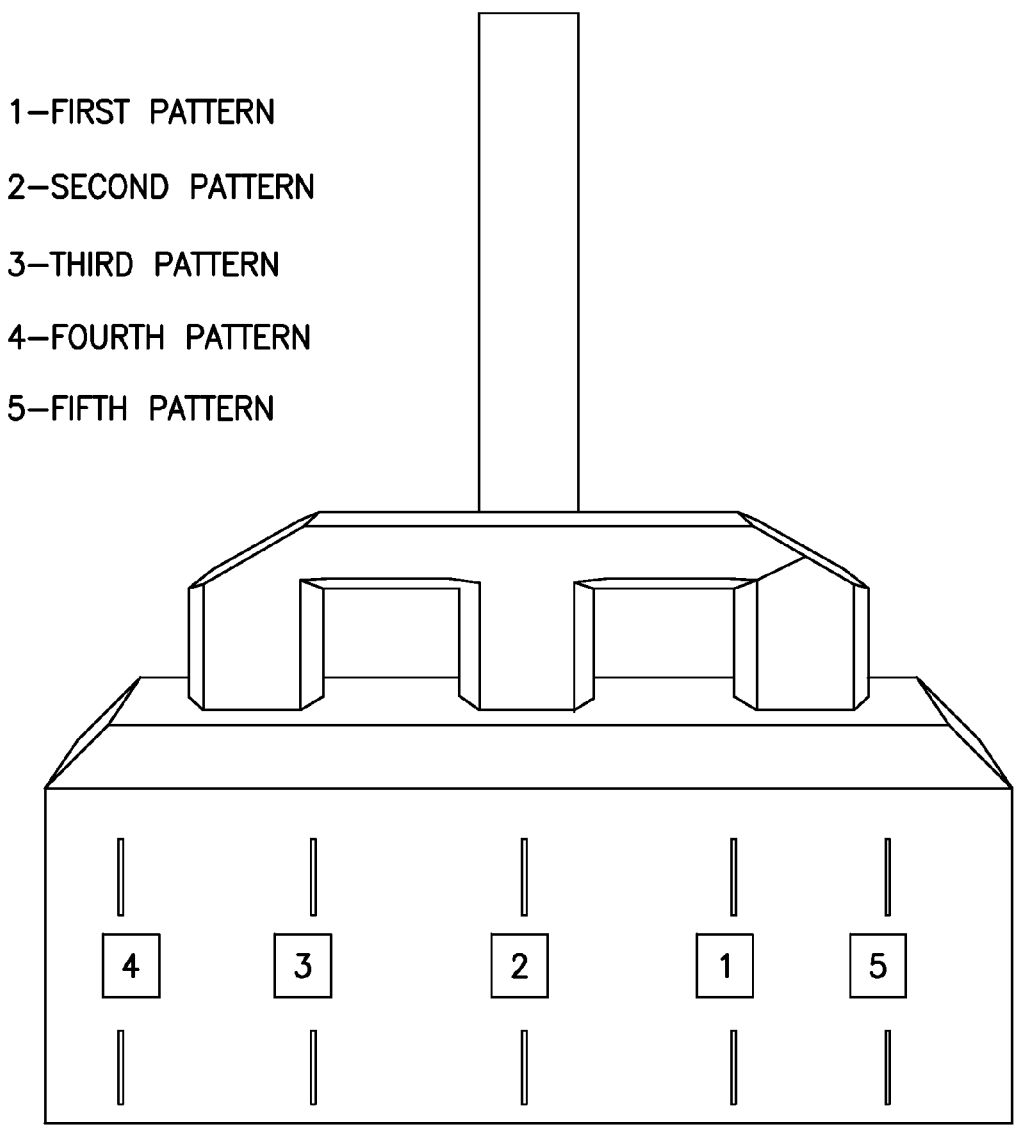
FIG. 6 depicts the small top and bottom instruments position (i.e. probe T and probe B, respectively), by pattern.

After completing the above measurements the relative position of the instruments to the anode surface was changed, by assembling the four instruments in a different pattern. A total of five different patterns were used, and for each pattern all the above described measurements were taken again on both, green and baked anodes. The positions of the four point probe instruments relative to the anode surface are shown in FIGS. 4, 5 and 6.

Given the anode geometry, five different locations for the vertical instruments were included in the experiment, whereas for the horizontal instrument only three locations were considered. Details regarding the distance between the probes and the electric current used for each probe, on both green and baked anodes are presented in the Table II below.

TABLE II

Instruments' geometry and electric current used for both anode types

| Probe | Distance between current points | Distance between potential points | Green anode current I (A) | Baked anode current I (A) |
|---|---|---|---|---|
| Horizontal | 56" | 54" | 5 | 20 |
| Vertical | 12" | 9" | 5 | 20 |
| Small top | 3.75" | 2.25" | 5 | 20 |
| Small bottom | 3.75" | 2.25" | 5 | 20 |

Figure 7:
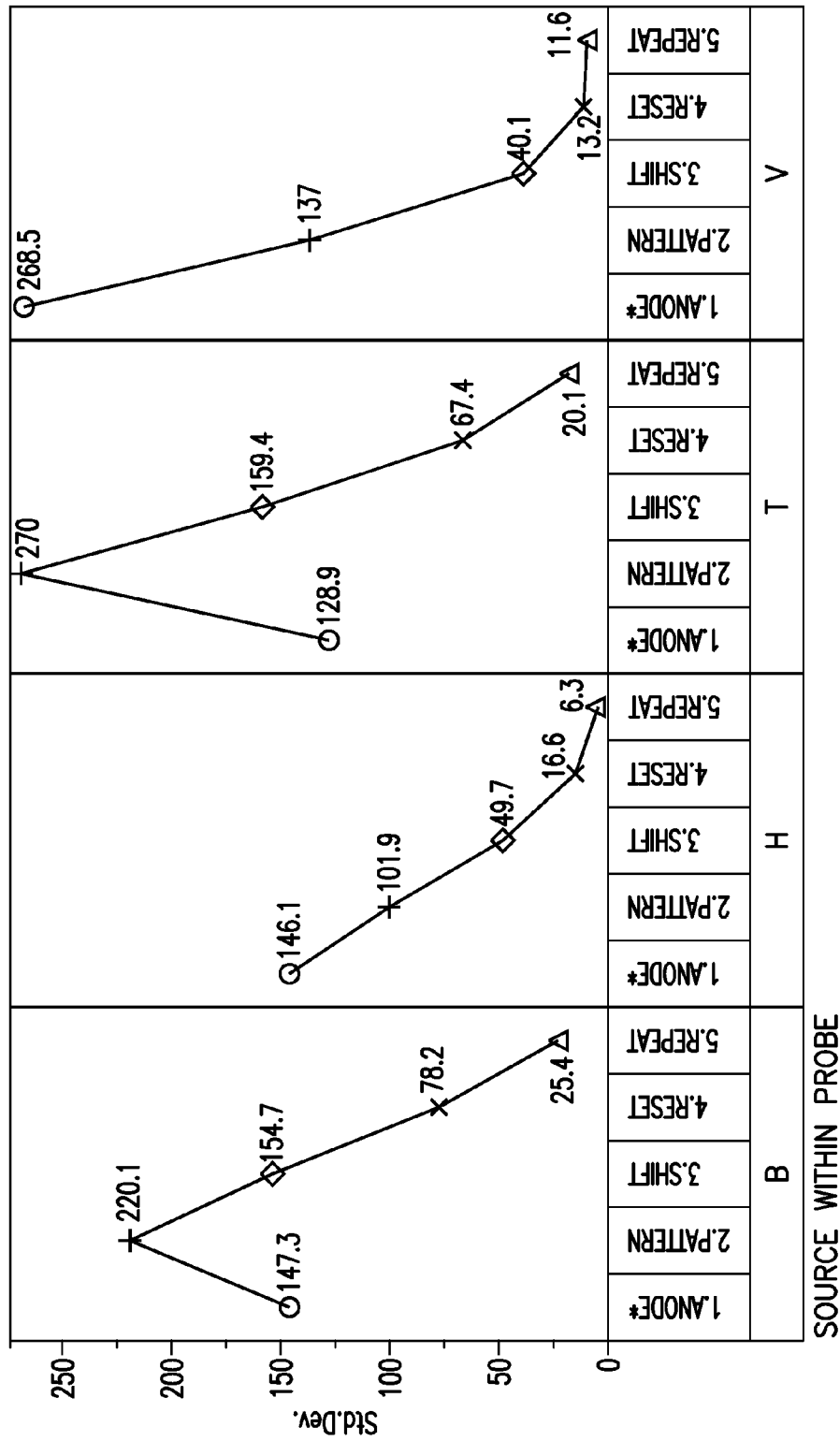
FIG. 7 depicts the variability chart for standard deviation by measurement, for each probe, on green anodes.
Figure 8:
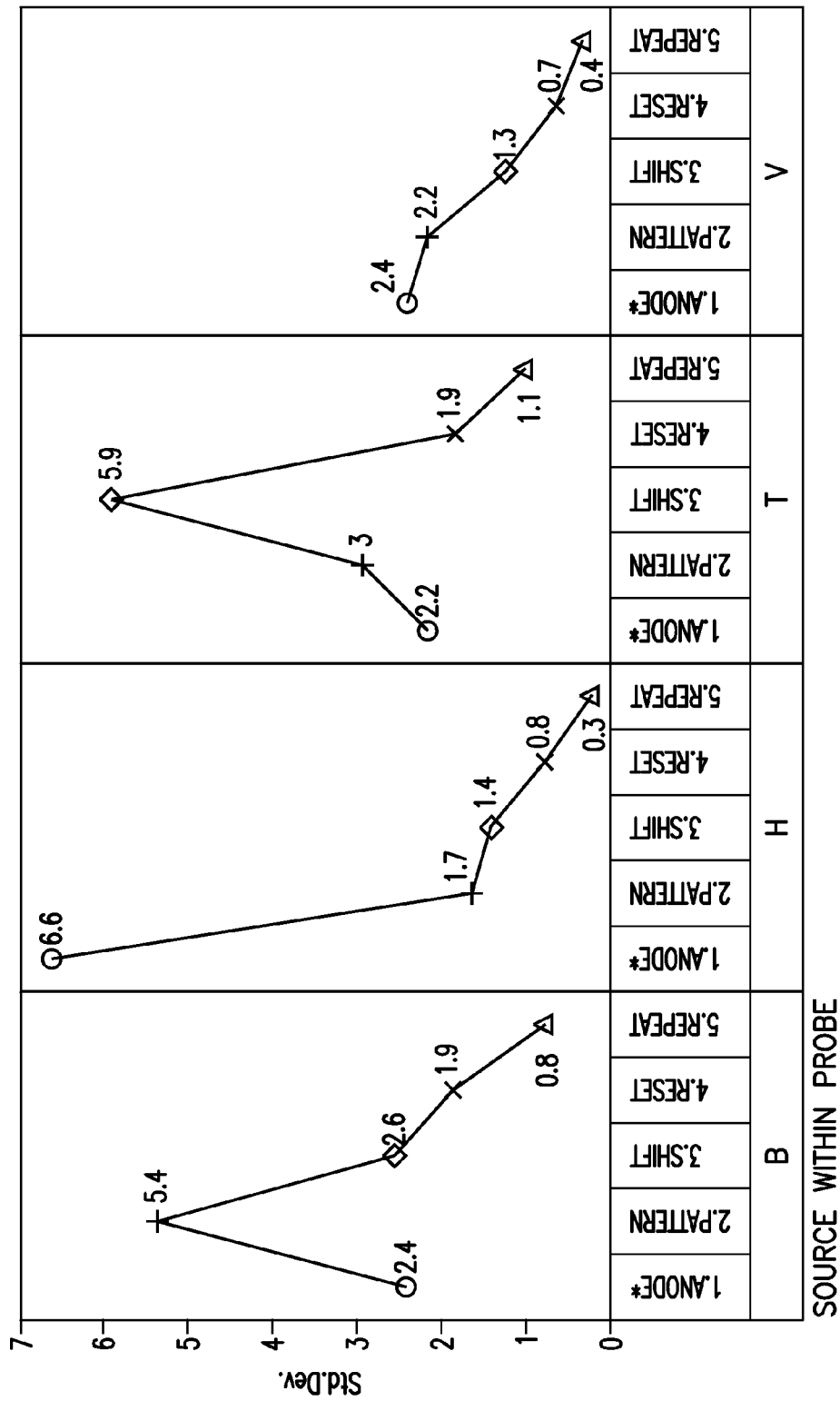
FIG. 8 depicts the variability chart for standard deviation by measurement, for each probe, on baked anodes.

All the voltage drop measurements were converted into electrical resistivity values, using the correction factors detailed above. These values were used to estimate the variance components of the measurements. Without being bound to a particular mechanism or theory, it was assumed that the four point probe instrument precision can be characterized by measurement standard deviation ranking. This analysis was performed by using the statistical software JMP. The standard deviations associated with the repeat, reset and pattern measurements (described above) are presented in FIG. 7 for the green anodes and FIG. 8 for the baked anodes. In addition, the anode standard deviation is also shown in these plots, which basically characterizes the variability between the anodes and is calculated as the standard deviation of the per anode means (all measurements included).

It is noted that the anode variation and the pattern variation compete as the largest source of variation, depending on probe and anode states, baked vs. green. There is one exception to this, the small top instrument measurements on baked anodes. Reset and repeatability standard deviations are low relative to the other sources. Without being bound to a particular mechanism or theory, this indicates that the instruments can be used to detect within the anode and between anodes differences due to assignable causes. In addition, the larger probes, H and V, show lower reset and repeatability variation than the smaller instruments, T and B. Without being bound to a particular mechanism or theory, due to the believed heterogeneity of the anodes, this result was expected.

Example 4

Comparison of Core Instrument to Instrument of Example 2

In this example, the standardized measurement's precision on measuring electrical resistivity of baked cores was compared to the precision of the device of Example 2. In order to do this, the total test errors were calculated. This was computed as the statistical sum of the repeatability and reproducibility. In one embodiment, for a possible in-line automated measurement system, the reproducibility term is calculated from measurements taken at the same location within short order, with the instrument pulled back, then re-positioned onto the same anode. This is basically setup reproducibility, and the customary measurement of the same material by a different operator using a different instrument has little relevance for this application. Based on the above, the total test errors have been calculated and the results are presented in Table III.

TABLE III

Total test error and coefficient of variation, by probe.

| Probe | Repeatability | Reproducibility | Total test error | LSD | Median resistance | CV |
|---|---|---|---|---|---|---|
| Baked Anode Measurements | | | | | | |
| Horizontal | 0.27 | 0.85 | 0.9 | 1.8 | 53.93 | 1.7 |
| Vertical | 0.37 | 0.76 | 0.8 | 1.7 | 54.14 | 1.6 |
| Small Top | 1.09 | 2.16 | 2.4 | 4.8 | 39.71 | 6.1 |
| Small Bottom | 0.84 | 2.06 | 2.2 | 4.4 | 42.91 | 5.2 |
| Std. Core Inst. | 1.2 | 1.5 | 1.9 | 3.8 | | |
| Green Anode Measurements | | | | | | |
| Horizontal | 6.29 | 17.76 | 18.8 | 37.7 | 1997.33 | 0.9 |
| Vertical | 11.58 | 17.53 | 21.0 | 42.0 | 2004.36 | 1.0 |
| Small Top | 20.11 | 70.33 | 73.1 | 146.3 | 1551.82 | 4.7 |
| Small Bottom | 25.39 | 82.2 | 86.0 | 172.1 | 1760.47 | 4.9 |

The total test error for the two larger probes (H, V) appears to be roughly half of that of the standard core instrument. The smaller probes (T, B) show a slightly inferior test error. Without being bound to a particular mechanism or theory, one explanation is that these measurements were taken manually, and may have lacked a consistent pressure on the contact points. Thus, based on this comparison, it is expected that even the smaller probes are going to be at least as good as the current standard core measurement instrument from a precision point of view.

For measurements on the green anode there is no standardized method for reference. Instead, calculating the coefficient of variability, CV, a direct comparison between the precision of these instruments on the two different anode states can be made. The CV values for the measurements on both, green and baked anodes are also presented in Table III. It can be seen that the measurement precision on the green anodes is superior to the precision on the baked anodes. The calculation of the least significant difference, LSD, is also provided in Table III, and will be useful in analyzing differences between anodes in future designs of experiment.

These electrical resistivity measurements were plotted and it was determined that the patterns appeared to be random in comparing anode-to-anode. Thus, at least for the 22 anodes tested, there was no pattern revealed regarding a consistent anode electrical resistivity print based on the anodes being from the same manufacturing line/location.

Example 5

Baked and Green Anode Electrical Resistivity Measurements

At an anode manufacturing location, measurements were taken on 30 baked anodes and 10 green anodes using an electrical resistivity device as set forth in Example 1. It was determined that the response of the four point probe depends upon the geometry of the surface to which it is applied. If the surface is generally concave, the measured voltage drop will be higher than for a flat surface, and vice-versa. Consequently, a geometry-specific correction factor is needed to properly calculate the resistivity from the measured voltage. The correction factor was approximated for each measurement location using finite element simulation of the measurement procedure.

Figure 9:
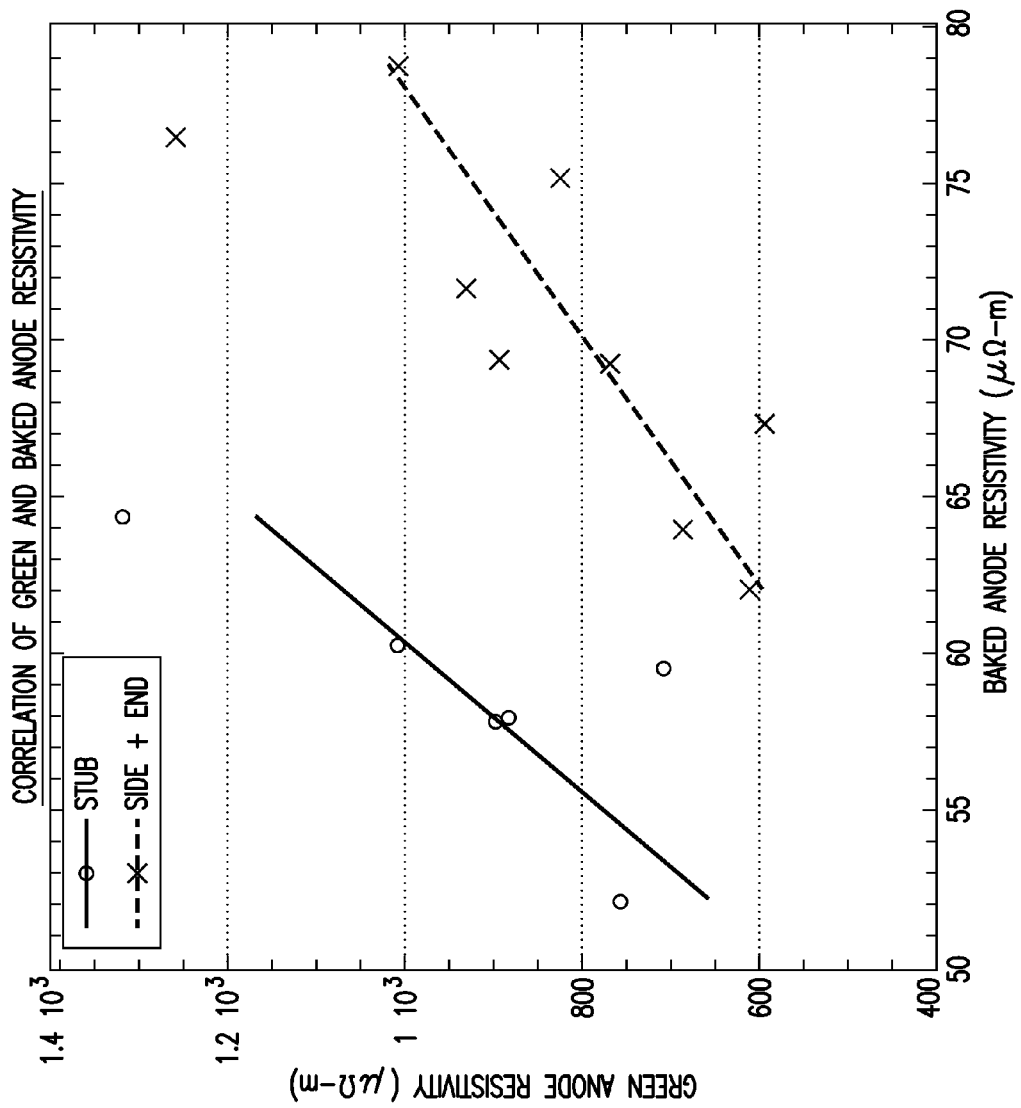
FIG. 9 is a graph depicting the correlation of green and baked anode electrical resistivity.
Figures 11, 12:
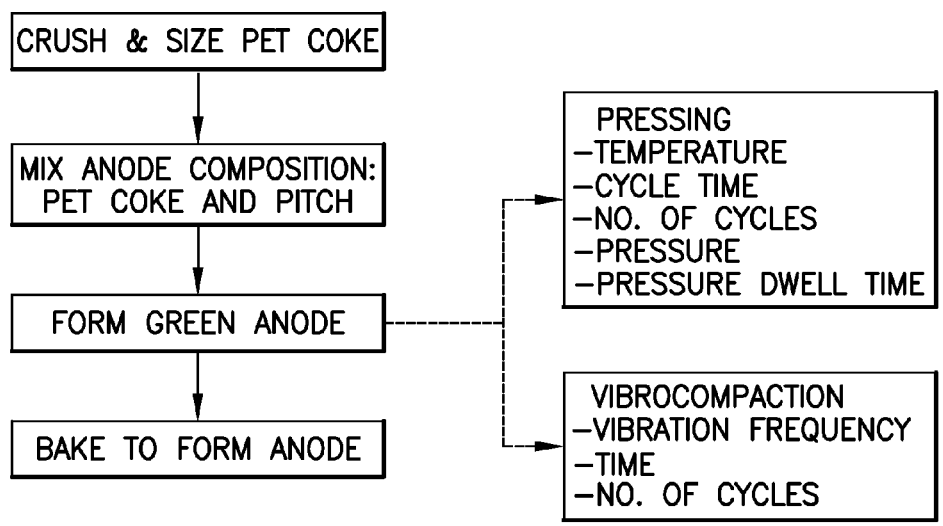
FIG. 11 is a table depicting the coefficient variation of electrical resistivity measurements for different locations on baked vs. green anodes.
FIG. 12 is a schematic of an anode manufacturing process.

Without being bound to a particular mechanism or theory, it appears that fairly good correlations exist between the two, although the results should be grouped: the correlation near the stub-hole is different from that on the sides and ends of the anodes. This is more clearly shown in FIG. 9, FIG. 10 depicts the resistivity for both the baked and green anodes. FIG. 11 depicts the coefficient of variation for the baked and green anode measurements. Referring to FIG. 11, the CV is higher for the green anode measurements. Without being bound to a particular mechanism or theory, this was expected as the pitch is essentially non-conductive, so that in the green anodes, conductivity was limited to contacts between the coke particles. Thus, it is believed that measuring the electrical resistivity in the green anodes will provide a more sensitive measure of the structural variations brought about by the anode manufacturing process. One source of possible error in these measurements of FIGS. 10 and 11 is the manual indexing of these small scale measurements may have resulted in a lower overall precision, or a calculation error may have resulted from a typographical error with the current amperage of the green anodes.

Example 6

Electrical Resistivity as a Function of Pitch Content in Anode Composition

Figure 16:
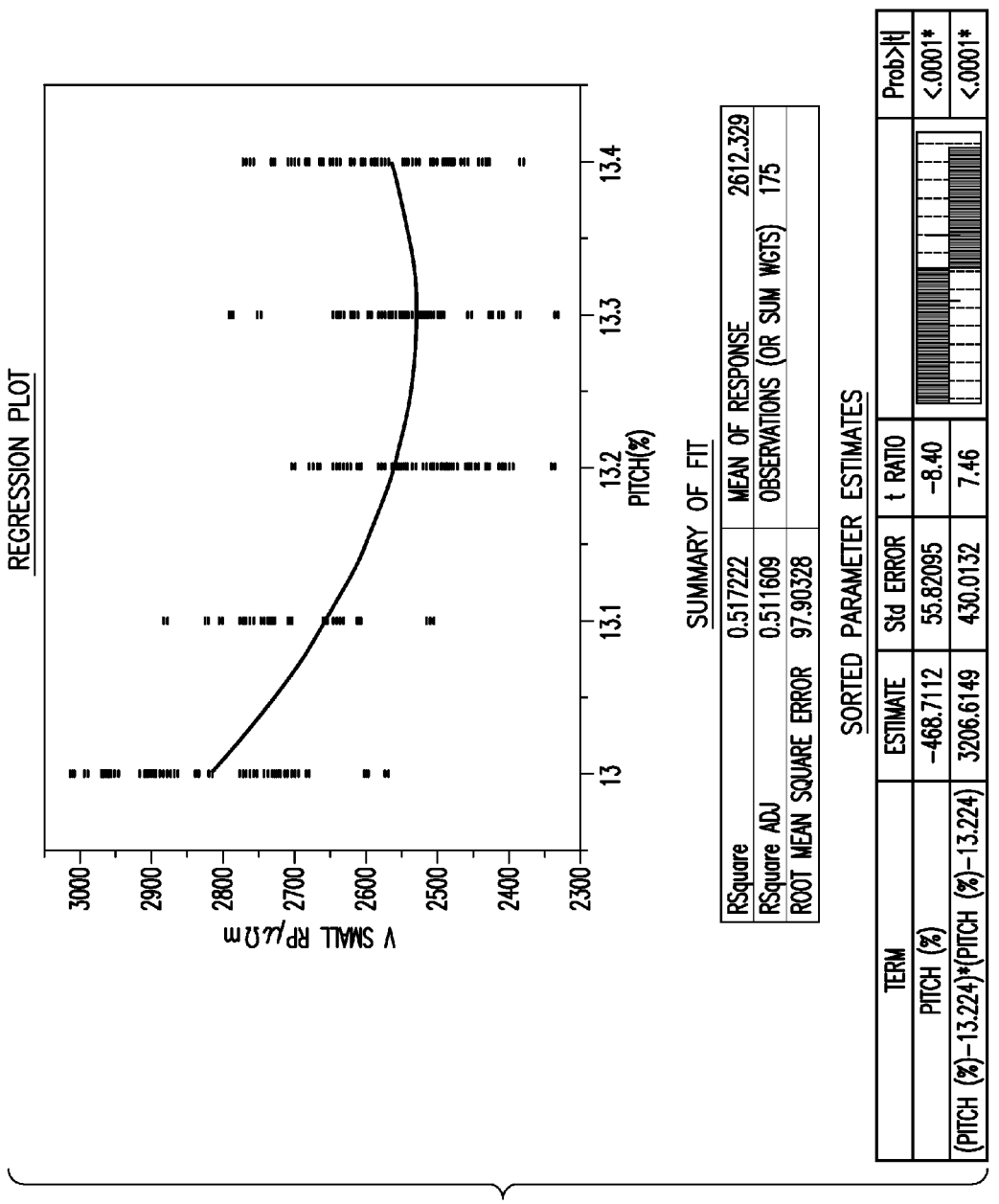
FIG. 16 is a graph depicting experimental data of the resulting electrical resistivity variation in green anode depicted as a function of pitch content (wt. %).

Referring to FIG. 16, a number of measurements have been conducted on green anodes (carbon material), with pitch as the only variable. The pitch variation was limited to 0.1% increments. These tests were completed on different days, and using different dry aggregate recipes. Each anode was measured in eight different locations with electrical resistivity devices retained in different locations with an electrically insulated frame. For each location, the electrical resistivity measurement generated a curve as the one shown in FIG. 16. For each curve, the minimum electrical resistivity measurement was at or very close to the optimum pitch level in anodes. The obtained curves for each series of measurements were approximately parallel. However, the electrical resistivity values (absolute values), including the minimums, were different. Without being bound by a particular mechanism or theory, this is believed to be based on some factors, including: measurement location and recipe used for each anode. Without being bound by a particular mechanism or theory, these findings are indicative that in-line electrical resistivity measurements on green anodes provide a useful feedback to the process with respect to varying the anode composition (i.e. changing the pitch to coke ratio to optimize pitch content in an anode composition for a given anode production process).

Example 7

Heterogeneity Measurements on Green Anodes

Figures 17, 17A:
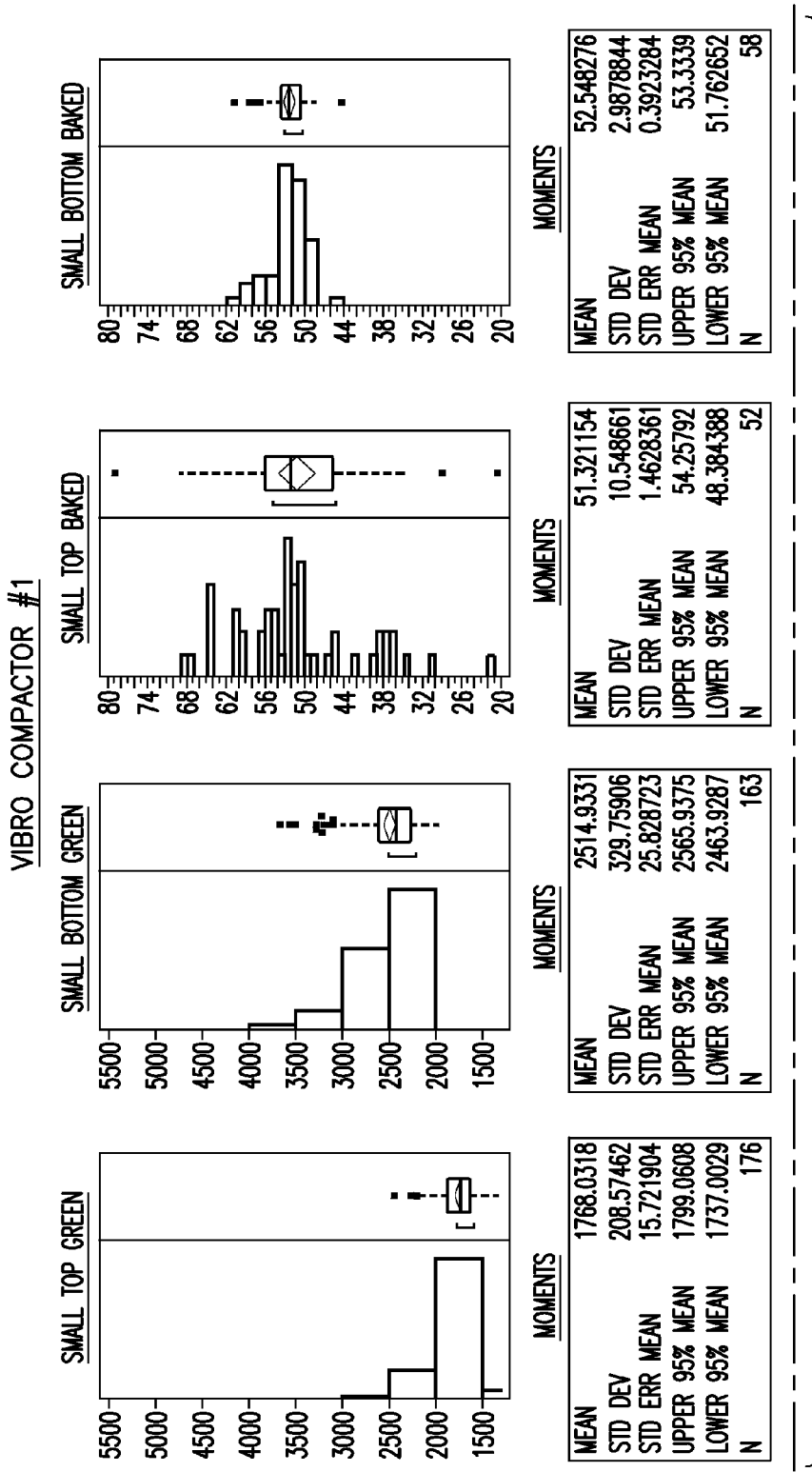
FIG. 17 is a graph depicting experimental data depicting the differences which result in the green anodes (depicted as small top and small bottom measurements along an anode surface), based on differences in the forming parameters (e.g. two different vibrocompactors were utilized) as compared to after baking the anodes.
Figure 17B:
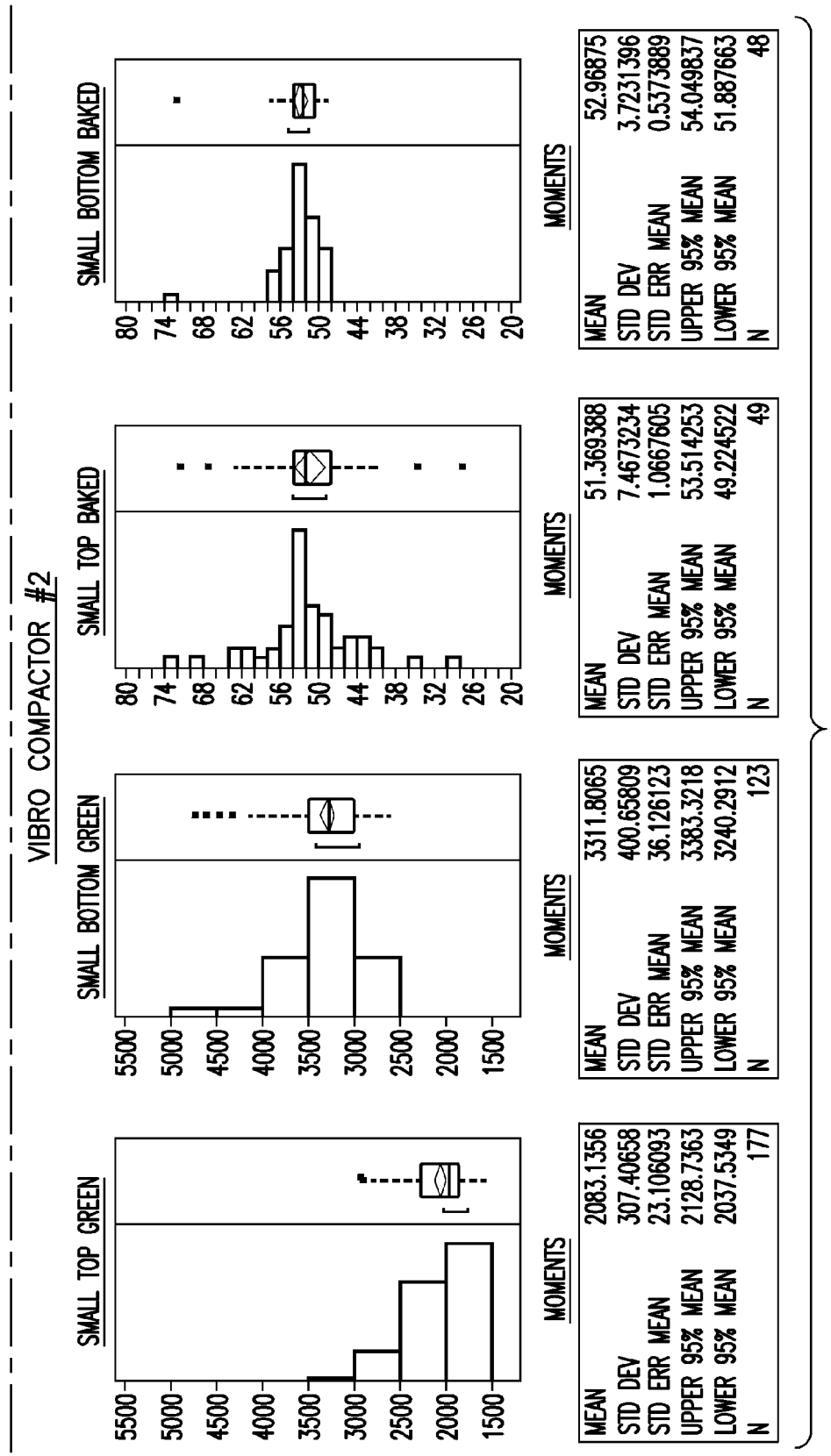

Referring to FIG. 17, a series of electrical resistivity measurements were taken on green anodes after forming (i.e. where forming was vibocompaction on one of two vibrocompactors) and after baking. Electrical resistivity measurements were taken along a top and bottom of the long side of each green anode in order to evaluate anode heterogeneity due to vibrocompaction and to observe how baking impacted the electrical resistivity measurements. Though some anodes were tracked through the process (i.e. after forming the green anode through baking to form the final, baked anode), a number of anodes were not sufficiently tracked through the process, which resulted in a larger sample size of green anodes after forming than the sample size for baked anodes after baking.

The graphs depicted in FIG. 17 illustrate the anode heterogeneity in the forming process and after the baking process, as exposed by the electrical resistivity measurements (all measurements in $\mu\Omega m$). With reference to FIG. 17, it is noted that all four top measurements are smaller than any of the four bottom measurements. Also, it is noted that all of the electrical resistivity measurements on compactor #1 are smaller than the equivalent ones on compactor #2. For the baked anodes, the differences are not significant.

All four measurements taken at the top of the anode (T), two on the green anodes and two on the baked ones, are smaller than any of their respective bottom measurements, regardless of the compactor on which the anodes were produced. Without being bound by a particular mechanism or theory, this may be attributable to the forming process (e.g. friction with the mold, unequal compaction, etc). The distribution and the simple statistics of all these measurements are presented in FIG. 17.

Also, it is noted that all the measurements taken on the anodes made on compactor #1 are smaller than the equivalent measurements taken on compactor #2. However, this difference is not as observable in the baked anodes, and was confirmed that the difference is not statistically different. Without being bound by a particular mechanism or theory, the electrical resistivity measurements resulted in top to bottom differences which are believed to be compactor dependent. Also, FIG. 17 is confirmation via electrical resistivity measurements in that the baking process appears to reduce: the differences in electrical resistivity between the top and the bottom, as well as the differences resulted from the compaction on the two different compactors.

Prophetic Example Method of Optimizing Pitch via Electrical Resistivity In one embodiment, a method is provided for making green anodes, where the electrical resistivity measurements are utilized in order to optimize the amount of pitch in the anode composition (e.g. pitch to coke).

The method provides: forming a first green anode from an anode composition having a first pitch content, the first anode having a first electrical resistivity; forming a second green anode, the anode composition having a second pitch, the second anode having a second electrical resistivity, where the second pitch is different than the first pitch (e.g. higher or lower pitch wt. %), and obtaining the first electrical resistivity and the second electrical resistivity (e.g. from a measured voltage drop from which the measured electrical resistivity is measured); and comparing the first electric resistivity to the second resistivity.

In some embodiments, if the first electrical resistivity is lower than the second electrical resistivity, revert to the first pitch content of the anode composition.

In some embodiments, if the first electrical resistivity is lower than the second electrical resistivity, the method comprises forming a third green anode, the anode composition having a third pitch, the third anode having a third electrical resistivity, where the third pitch is different from the first pitch and closer to the first pitch wt. % than the second pitch wt. %, and reiterate the previous steps, but for this variation (i.e. obtaining resistivities, and comparing the resistivities as set out above, to generate an action—change pitch (increase or decrease) or maintain pitch).

In some embodiments, if the first electrical resistivity is higher than the second electrical resistivity, revert to the second pitch content (wt. %) of the anode composition.

In some embodiments, if the first electrical resistivity is higher than the second electrical resistivity, the method comprises forming a fourth green anode, the anode composition having a fourth pitch, the fourth anode having a fourth electrical resistivity, where the fourth pitch is different from the second pitch and is closer to the second pitch than the first pitch wt. %, and reiterate the previous steps, but for this variation (i.e. obtaining resistivities, and comparing the resistivities as set out above, to generate an action—change pitch (increase or decrease) or maintain pitch).

It is noted that while first, second, and third anodes are called out above, first anode is also understood to refer to a first group of anodes (second anode as second group of anodes, third anode as third group of anodes, fourth anode as fourth group of anodes, and so on), with the electrical resistivity measurements referring to a statistical summary of the same for the corresponding group (e.g. mean value, mean square value, median value, etc.).

In some embodiments, the second pitch is higher than the first pitch, so the third pitch is selected to be lower than the first pitch. In some embodiments, the second pitch is lower than the first pitch, so the third pitch is selected to be higher than the first pitch. Based on the trend depicted in FIG. 16, an iterative change in pitch content (followed by wt. %) and electrical resistivity measurement can be used to determine the optimum pitch for an anode production process operation, for that particular formulation, equipment set up, and anode composition (e.g. butt content, percent of volatiles in the pitch, % granulometry, etc.).

Prophetic Example

Method of Monitoring of Anodes and Adjusting Anode Production Process

In one embodiment, electrical resistivity measurements are taken from anodes at least one of various locations along the anode production process. In one embodiment, electrical resistivity measurements are taken on each (or a group of) green anodes immediately after forming (while still hot from forming process). In one embodiment, electrical resistivity measurements are taken on each (or a group of) green anodes immediately after cool down from the forming step.

In some embodiments, if the electrical resistivity of the green anodes are within the target electrical resistivity (e.g. at the minimum, at the maximum, below a certain threshold, above a certain threshold, within a range, outside of a range, or a combination thereof), no adjustment is needed (e.g. such that in lieu of adjusting, the method comprises a repeat step to continue determining electrical resistivity and continue correlating the same against the target electrical resistivity to monitor whether an adjustment is needed).

In some embodiments, each anode (green or baked) is lifted from the production line via a stand (e.g. made of electrically insulated materials) and configured to measure the electrical resistivity via an electrical resistivity device or permit such device(s) with accompanying frame to measure the same. In some embodiments, the frame is adjustable. In some embodiments, the frame is rigid. In some embodiments, each anode (green or baked) is rolled onto electrically insulated materials (e.g. plastic rollers, non-conductive rollers) that are located in-line in order to obtain electrical resistivity measurements.

Referring to FIG. 12, an exemplary flow path of anode production is depicted. Referring to FIG. 12, coke is crushed and sized into the appropriate size fraction(s). Some recipes for the anode composition call for various sized fractions (e.g. course, intermediate, fine, extra-fine), some for two or more (e.g. three, four) different size fractions of coke.

After the coke is crushed and sized, the anode composition is mixed, with a ratio of coke to pitch. The ratio of coke to pitch (and/or binder content) impacts the resulting anode quality. In some embodiments, the composition includes: coke and pitch (either coal tar or petroleum pitch, or a mix); and/or optional additives. Some non-limiting examples of additives include: paste scrap, or green anode scrap, recycled crushed used anodes, also known as anode butts, and combinations thereof. The composition (first composition) is mixed to combine or blend the components. Non-limiting examples of mixing include: mechanical stirrers, shaking the vessel holding the composition, or other stirring mechanisms to combine the components. In some embodiments, depending on the ratio of coke to pitch, the mixing energy (frequency, mixing time, etc) is adjusted (increased or decreased) such that the resulting mixture is blended (e.g. homogeneously).

After the composition is mixed, a green anode is formed from the composition. As some non-limiting examples for forming, the green anode can be pressed or vibrocompacted into the green anode form. In some embodiments, the vibrocompactor includes additional components which are configured to apply pressure to certain parts of the compactor.

Once the green anode is formed, the resulting green anode is baked (e.g. in an oven) in order transform the green anode of a first composition into a monolithic block of coke. In some embodiments, the baking step removes volatile components present in the green anode and further densifies the anode components (e.g. increasing the real density, reducing the electrical resistivity).

Figure 13:
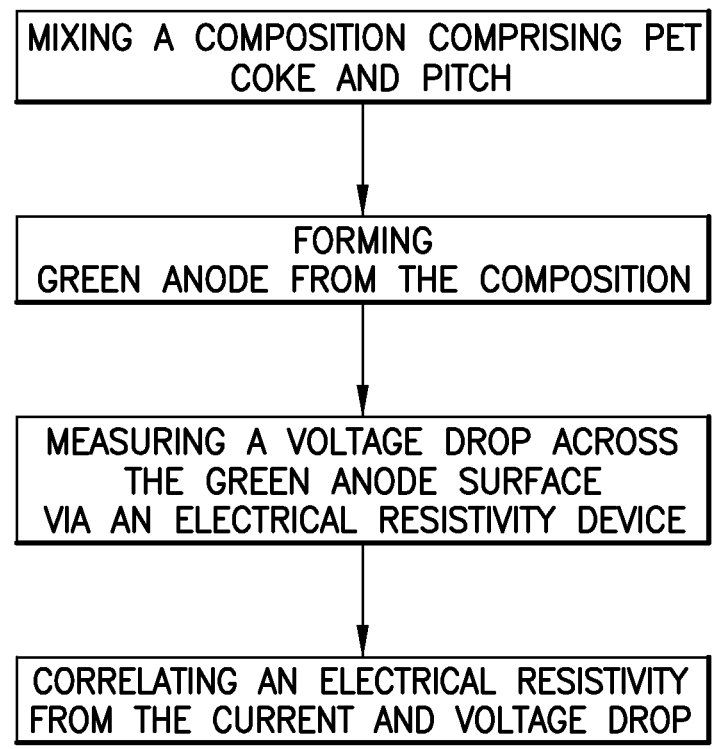
FIG. 13 is a schematic of an anode manufacturing process in accordance with the instant disclosure.

Referring to FIG. 13, a method is depicted, comprising: mixing a composition comprising coke and pitch; forming a green anode from the composition; measuring one or more voltage drop across the green anode surface via an electrical resistivity device; and correlating one or more electrical resistivities from the current and voltage drop.

Figure 14:
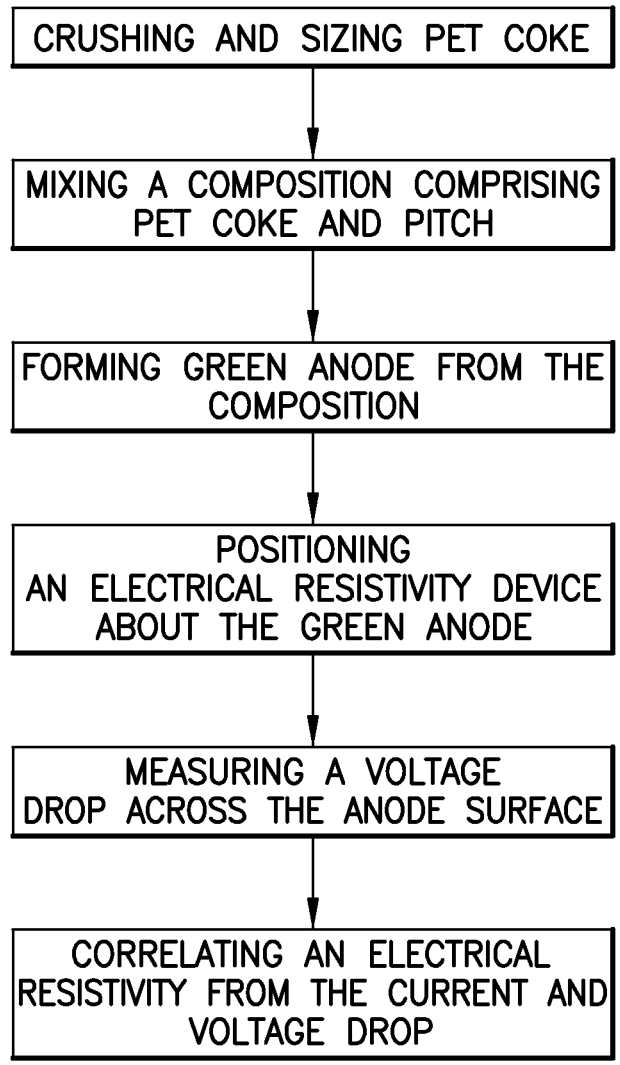
FIG. 14 is a schematic of an anode manufacturing process in accordance with the instant disclosure.

Referring to FIG. 14, a method is depicted, comprising: crushing and sizing the coke; mixing a composition comprising coke and pitch; forming a green anode from the composition; positioning an electrical resistivity device about the green anode (e.g. along the surface of the green anode to define at least one electrical current path); directing current across the anode surface between two current probes of the device; and measuring one or more voltage drop(s) across the anode surface via two electrical probes (e.g. wherein the electrical probes are located between the current probes and in spaced relation from each other); and correlating one or more electrical resistivities from the current and voltage drop. In some embodiments, the anode surface comprises a top, a bottom, a side, across a corner, across a stub hole, inside of a stub hole (e.g. in the flutes, or internal ridges of the stub hole, and/or the depressions in the stub hole), etc.

Figure 15:
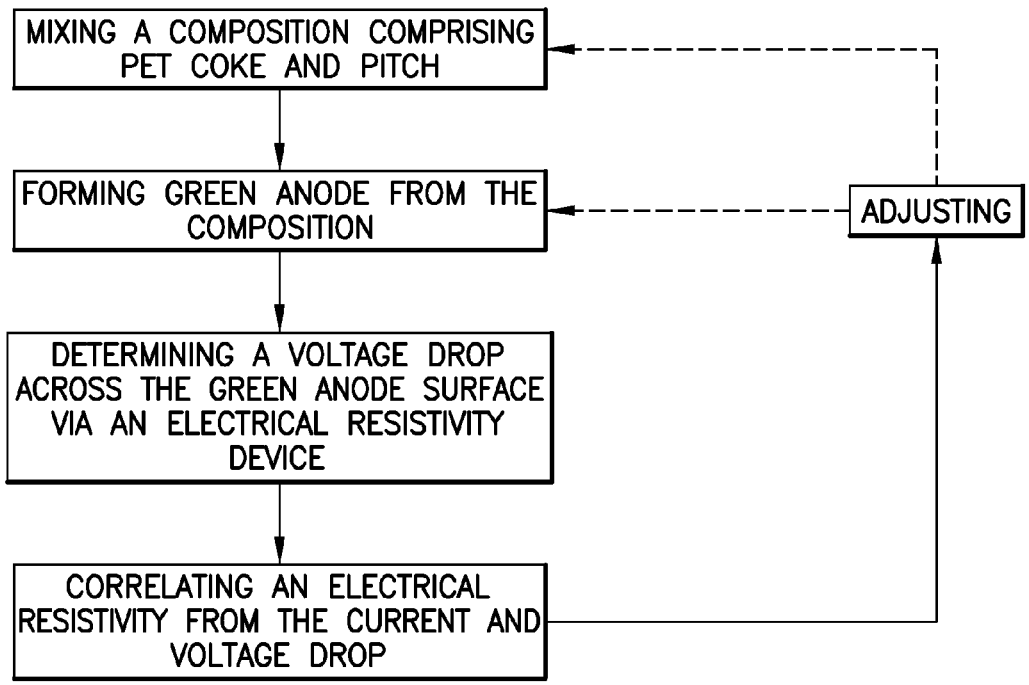
FIG. 15 is a schematic of an anode manufacturing process in accordance with the instant disclosure.

Referring to FIG. 15, in some embodiments, one or more of the aforementioned methods include the step of comparing the measured electrical resistivity to a target electrical resistivity. In some embodiments, one or more of the aforementioned methods comprise the step of adjusting, based on the comparing step, at least one of the anode production parameters: e.g. the mixing step or the forming step.

In one embodiment, adjusting comprises changing the coke to pitch ratio. In one embodiment, the adjusting step comprises increasing the amount of coke relative to the amount of pitch in the composition (e.g. a second composition, which is different than the first composition). In one embodiment, the adjusting step comprises decreasing the amount of coke relative to the amount of pitch in the composition (e.g. a second composition, which is different than the first composition).

In one embodiment, the adjusting step comprises increasing the mixing time, mixing rpm (e.g. with a stirrer or stir bar), or amount of agitation via mixing.

In one embodiment, the adjusting step comprises changing the anode granulometry (e.g. changing the ratio of coke fractions, including the amount of coarse, fine, and/or super fine materials).

In some embodiments, the adjusting step comprises: changing one or more of the forming parameters; increasing the pressure during the forming (e.g. pressing) step; decreasing the pressure during the forming (e.g. pressing) step; increasing the dwell time during the forming step; decreasing the dwell time during the forming step; increasing the number of pressing cycles; decreasing the number of pressing cycles; increasing the vibration frequency of the vibrocompactor; decreasing the vibration frequency of the vibrocompactor; and combinations thereof.

In some embodiments, based on the comparing step, the method comprises, setting a baking step in accordance with the green anode resistivity. In some embodiments, the baking step comprises: increasing the bake time, decreasing the bake time, increasing the bake temperature, decreasing the bake temperature, or positioning the green anode differently within the oven (e.g. different heat flux at center vs. ends of oven) in accordance with the green anode resistivity measurement in order to provide a final baked anode with a desired electrical resistivity and density.

In some embodiments, for one or more of the aforementioned methods, one or more of the crushing and sizing; mixing; forming; positioning; measuring; correlating; comparing; and adjusting steps are completed in an automated manner (e.g. via a feedback loop on a computer and an automated assembly line of an anode manufacturing process).

As detailed herein, in some embodiments, a specifically designed computer is configured to receive multiple electrical resistivity measurements from a green electrode (e.g. anode) and incorporate the measurements in order to provide an anode map (e.g. depicting inhomogeneities) indicative of the anode quality (high, medium, low, pass/no pass).

In some embodiments, a specifically designed computer is configured to monitor (monitoring) an anode production process by comparing electrical resistivity measurement(s) obtained for each anode (or group of anodes) in a production process (e.g. after forming green anode while still warm, after cooling the green anode as it exits from the forming process, and/or after baking to transform the green form into the final, baked anode), and if the measured electrical resistivity values are not within the target electrical resistivity values, adjust the production process (e.g. adjust the anode processing parameters: anode composition, anode mixing process, anode forming process, or anode baking process). In some embodiments, the specifically programmed computer operates in a continuous, real-time process monitoring and adjusting, if necessary, the anode production process. In some embodiments, the specifically programmed computer operates in a periodic, real-time process in monitoring and adjusting, if necessary, the anode production process. In some embodiments, the specifically designed computer is configured to monitor/review historical anode data (e.g. electrical resistivity measurements) in order to identify equipment to be serviced and/or replaced, or to evaluate operator performance. In some embodiments, the specifically designed computer is configured to correlate performance data of the final baked anodes with the data for the anodes produced in a particular production line to identify additional improvements and/or variables in processing parameters and anode characteristics.

Computer architecture: The inventive computer methods and the computer systems/machines of the instant invention utilize various computer machines. However, not all of these computer machines may be required to practice the invention, and variations in the arrangement and type of the components may be made without departing from the spirit or scope of the invention. In some embodiment, the computer systems/machines of the instant invention host a large number of members and concurrent transactions. In other embodiments, the computer systems/machines of the instant invention are based on scalable computer and network architectures that incorporate varies strategies for assessing the data, caching, searching, and database connection pooling.

In one example, the exemplary scalable architecture is an architecture that is capable of operating multiple servers. In some embodiments, the computing system/machines in accordance with the instant invention may include, but not limiting to, one or more programmed computers, systems employing distributed networking, or other type of system that might be used to transmit and process electronic data. In some embodiments, client devices (e.g., computers, mobile device, etc.) of AOS's users include virtually any computing device capable of receiving and sending a message over a network to and from another computing device, such as servers, each other, and the like.

In some embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices are any device that is capable of connecting using a wired or wireless communication medium such as a PDA, POCKET PC, wearable computer, and any other device that is equipped to communicate over a wired and/or wireless communication medium.

In some embodiments, the client devices are further configured to receive a message from the another computing device employing another mechanism, including, but not limited to email, Short Message Service (SMS), Multimedia Message Service (MMS), instant messaging (IM), internet relay chat (IRC), mIRC, Jabber, and the like.

In some embodiments, the utilized networks can be configured to couple one computing device to another computing device to enable them to communicate. In some embodiments, the exemplary networks are enabled to employ any form of computer readable media for communicating information from one electronic device to another. Also, in some embodiments, the networks can include a wireless interface, and/or a wired interface, such as the Internet, in addition to local area networks (LANs), wide area networks (WANs), direct connections, such as through a universal serial bus (USB) port, other forms of computer-readable media, or any combination thereof. In some embodiments, on an interconnected set of LANs, including those based on differing architectures and protocols, a router acts as a link between LANs, enabling messages to be sent from one to another. Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art.

Furthermore, in embodiments, remote computers and other related electronic devices could be remotely connected to either LANs or WANs via a modem and temporary telephone link. In essence, in some embodiments, the exemplary network can includes any communication method by which information may travel between client devices and servers.

In some embodiments, each of the client devices (e.g., computers, mobile device, smart routers, etc.) comprises a computer-readable medium, such as a random access memory (RAM) coupled to at least one processor. In some embodiments, the processor executes computer-executable program instructions stored in non-transient memory. Such processors comprise a microprocessor, an ASIC, and state machines. Such processors comprise, or are be in communication with, media, for example computer-readable media, which stores instructions that, when executed by the processor, cause the processor to perform the steps described herein.

Some embodiments of computer-readable media include, but are not limited to, an electronic, optical, magnetic, or other storage or transmission device capable of providing a processor with computer-readable instructions. In some embodiments, other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media transmit or carry instructions to a computer, including a router, private or public network, or other transmission device or channel, both wired and wireless. In some embodiments, the instructions comprise code from any computer-programming language, including, for example, C, C++, C#, Visual Basic, Java, Python, Perl, and JavaScript.

In some embodiments, the client devices also include a number of external or internal devices such as a mouse, a CD-ROM, DVD, a keyboard, a display, or other input or output devices. In some embodiments, examples of client devices are personal computers, digital assistants, personal digital assistants, cellular phones, mobile phones, smart phones, pagers, digital tablets, laptop computers, Internet appliances, and other processor-based devices. In general, a client device is any type of processor-based platform that is connected to a network and that interacts with one or more application programs of the instant invention. Client devices and AOS application can operate on any operating system capable of supporting a browser or browser-enabled application, such as Microsoft™, Windows™, or Linux. In some embodiments, the client devices include, for example, personal computers executing a browser application program such as Microsoft Corporation's Internet Explorer™, Apple Computer, Inc.'s Safari™, Mozilla Firefox, and Opera.

Of note, the embodiments described herein may, of course, be implemented using any appropriate computer system hardware and/or computer system software. In this regard, those of ordinary skill in the art are well versed in the type of computer hardware that may be used (e.g., a mainframe, a mini-computer, a personal computer ("PC"), a network (e.g., an intranet and/or the internet)), the type of computer programming techniques that may be used (e.g., object oriented programming), and the type of computer programming languages that may be used (e.g., C++, Basic, AJAX, Javascript). The aforementioned examples are, of course, illustrative and not restrictive.

While various embodiments of the present invention have been described in detail, it is apparent that modifications and adaptations of those embodiments will occur to those skilled in the art. However, it is to be expressly understood that such modifications and adaptations are within the spirit and scope of the present invention. While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A method, comprising:
   determining a measured voltage drop across a green anode surface via an electrical resistivity device positioned to contact the green anode surface;
   correlating a measured electrical resistivity from the voltage drop;
   comparing the measured electrical resistivity to a target electrical resistivity; and
   adjusting, based on the comparing step, at least one of anode processing parameters;
   wherein adjusting is selected from the group consisting of: changing a pitch to coke ratio; changing a mixing time; changing a mixing RPM; or changing an amount of agitation via mixing; changing the anode granulometry; changing one or more of the processing parameters; and combinations thereof.

2. The method of claim 1, wherein adjusting a processing parameter comprises:
changing:
a temperature; a cycle time; a pressure applied; a dwell time for pressure application, a vibration frequency, a vibration amplitude, a vacuum, a bellows pressure, and combinations thereof.

3. The method of claim 1, wherein the correlating, comparing, and adjusting step are completed via a specifically programmed computer.

4. The method of claim 1, wherein the method further comprises indicating a quality of the green anode via the measured electrical resistivity.

5. The method of claim 1, further comprising: indicating a green anode quality via a specifically designed computer.

6. A method, comprising:
mixing a first composition comprising:
an amount of coke and an amount of pitch;
forming a green anode in a mold having the first composition therein;
positioning an electrical resistivity device about the green anode to define at least one electrical current path, wherein the electrical resistivity device comprises:
at least two probes adapted to contact a portion of the anode surface of the anode and configured to measure the voltage drop across the current path; and
at least one electrical current source positioned in a spaced relation from the at least two probes, wherein the current source is adapted to contact another portion of the surface, wherein the current source is configured to transmit an electrical current from a current inlet through the anode body to the current outlet
determining a measured voltage drop across the green anode surface via the electrical resistivity device;
correlating an electrical resistivity from the current and the voltage drop across the at least one electrical current path;
comparing the measured electrical resistivity to a target electrical resistivity; and
adjusting, based on the comparing step, at least one of the mixing step or the forming step.

7. The method of claim 6, further wherein determining comprises: directing a current output of not greater than 5 amps from the current inlet to the current outlet.

8. The method of claim 6, wherein the forming step comprises:
pouring the first composition into a mold, and
pressing the first composition in the mold to form a green anode.

9. The method of claim 8, wherein the pressing step comprises vibrocompaction.

10. A method, comprising:
mixing a first composition comprising:
coke and pitch
forming a green anode in a mold having the first composition therein;
positioning a plurality of electrical resistivity devices about the green anode, wherein each electrical resistivity device is configured to contact an anode surface to define an electrical current path per each electrical resistivity device, wherein each electrical resistivity device comprises:
at least two probes adapted to contact a portion of the anode surface of the anode and configured to measure the voltage drop across the current path; and
at least one electrical current source positioned in a spaced relation from the at least two probes, wherein the current source is adapted to contact another portion of the surface, wherein the current source is configured to transmit an electrical current from a current inlet through the anode body to the current outlet;
determining a measured voltage drop across the anode surface for each electrical resistivity device;
correlating an electrical resistivity from the current and the voltage drop across the at least one electrical current path for each electrical resistivity device;
providing an anode map indicative of electrical resistivity which is compiled from the measured electrical resistivity measurements for various portions on the green anode;
wherein the positioning, correlating, determining, and providing steps are performed via a specifically programmed computer configured to be in electrical communication with the plurality of electrical resistivity devices;
indicating a green anode quality via the specifically designed computer; and
adjusting, based on the quality, at least one of the mixing step or forming step.

11. The method of claim 10, wherein positioning comprises: positioning at least four electrical resistivity devices onto an anode surface to obtain electrical resistivity measurements in a top, bottom, horizontal, and vertical direction along the anode surface.

12. The method of claim 10, wherein positioning further comprises positioning at least one of the plurality of electrical resistivity devices to provide an electrical resistivity measurement over two sides of the green anode via positioning one of the electrical probes and the current inlet orthogonally from the other electrical probe and the current outlet.

13. The method of claim 10, wherein the positioning step is across a corner of the green anode.

14. The method of claim 10, wherein the positioning step is across two opposing sides of the green anode.

15. The method of claim 10, wherein the positioning, correlating, determining, and providing steps are completed on green anodes in an anode production line.

16. The method of claim 10, wherein determining further comprises an electrical control system, which is configured to activate each of the plurality of electrical resistivity devices sequentially to obtain electrical resistivity measurements for each electrical resistivity devices on the green anode.

* * * * *